(12) United States Patent
Zhang et al.

(10) Patent No.: US 8,764,700 B2
(45) Date of Patent: Jul. 1, 2014

(54) SHEATH FOR USE WITH AN ULTRASOUND ELEMENT

(75) Inventors: John Zhang, Bothell, WA (US); Gary Lichttenegger, Woodinville, WA (US); James E. Rodriguey, Seattle, WA (US); Katsuro Tachibana, Fukuoka (JP)

(73) Assignee: Ekos Corporation, Bothell, WA (US)

( * ) Notice: Subject to any disclaimer, the term of this patent is extended or adjusted under 35 U.S.C. 154(b) by 0 days.

(21) Appl. No.: 13/332,226

(22) Filed: Dec. 20, 2011

(65) Prior Publication Data

US 2012/0089082 A1   Apr. 12, 2012

Related U.S. Application Data

(63) Continuation of application No. 11/418,491, filed on May 3, 2006, now abandoned, which is a continuation of application No. 10/369,270, filed on Feb. 18, 2003, now Pat. No. 7,413,556, which is a continuation of application No. 09/107,078, filed on Jun. 29, 1998, now Pat. No. 6,723,063.

(51) Int. Cl.
   *A61B 17/20* (2006.01)

(52) U.S. Cl.
   USPC .......................................... 604/22; 604/523

(58) Field of Classification Search
   USPC ................ 604/20–22, 96.01, 164.01, 523, 19
   See application file for complete search history.

(56) References Cited

U.S. PATENT DOCUMENTS

| | | | |
|---|---|---|---|
| 3,430,625 A | 3/1969 | McLeod, Jr. | |
| 3,565,062 A | 2/1971 | Kuris | |
| 3,827,115 A | 8/1974 | Bom | |
| 3,941,122 A | 3/1976 | Jones | |
| 4,040,414 A | 8/1977 | Suroff | |
| 4,192,294 A | 3/1980 | Gekhman et al. | |

(Continued)

FOREIGN PATENT DOCUMENTS

| | | |
|---|---|---|
| DE | 4005743 | 8/1991 |
| EP | 0 529 675 | 8/1992 |

(Continued)

OTHER PUBLICATIONS

Hynynen et al., "Small Cylindrical Ultrasound Sources for Induction of Hyperthermia Via Body Cavities or Interstitial Implants"; Arizona Cancer Center and Department of Radiation Oncology, University of Arizona Health Sciences Center; vol. 9, No. 2; pp. 263-274; 1993.

(Continued)

*Primary Examiner* — Kevin C Sirmons
*Assistant Examiner* — Phillip Gray
(74) *Attorney, Agent, or Firm* — Knobbe Martens Olson & Bear, LLP

(57) ABSTRACT

An apparatus for delivering ultrasound energy and a drug solution to a treatment site in a vessel is disclosed. The apparatus includes an elongate, hollow sheath having a distal opening and an energy delivery section at least partially constructed from a material that transmits ultrasound energy. The apparatus also includes a drug delivery lumen positioned along at least a portion of the sheath, the drug delivery lumen having at least one drug delivery port within the energy delivery section. The apparatus further includes an elongate body having an ultrasound element, the elongate body configured to be movably positioned within the sheath, such that ultrasonic energy can be transmitted from the ultrasound element through the energy delivery section.

33 Claims, 24 Drawing Sheets

(56) References Cited

U.S. PATENT DOCUMENTS

| | | | |
|---|---|---|---|
| 4,309,989 | A | 1/1982 | Fahim |
| 4,319,580 | A | 3/1982 | Colley |
| 4,354,502 | A | 10/1982 | Colley et al. |
| 4,531,943 | A | 7/1985 | Van Tassel et al. |
| 4,549,533 | A | 10/1985 | Cain et al. |
| 4,587,975 | A | 5/1986 | Salo et al. |
| 4,709,698 | A | 12/1987 | Johnston et al. |
| 4,750,902 | A | 6/1988 | Wuchinich et al. |
| 4,754,752 | A | 7/1988 | Ginsburg et al. |
| 4,808,153 | A | 2/1989 | Parisi |
| 4,821,740 | A | 4/1989 | Tachibana |
| 4,870,953 | A | 10/1989 | Donmicheal |
| 4,920,954 | A | 5/1990 | Alliger |
| 4,921,478 | A | 5/1990 | Solano et al. |
| 4,924,863 | A | 5/1990 | Sterzer |
| 4,951,677 | A | 8/1990 | Crowley et al. |
| 4,953,565 | A | 9/1990 | Tachibana et al. |
| 4,960,109 | A | 10/1990 | Lele |
| 4,971,991 | A | 11/1990 | Umemura et al. |
| 5,021,044 | A | 6/1991 | Sharkawy et al. |
| 5,059,851 | A | 10/1991 | Corl et al. |
| 5,069,664 | A | 12/1991 | Guess et al. |
| 5,088,499 | A | 2/1992 | Unger |
| 5,108,369 | A | 4/1992 | Ganguly et al. |
| 5,129,883 | A | 7/1992 | Black |
| 5,149,319 | A | 9/1992 | Unger |
| 5,163,421 | A | 11/1992 | Bernstein |
| 5,163,436 | A | 11/1992 | Saitoh et al. |
| 5,178,620 | A | 1/1993 | Eggers et al. |
| 5,185,071 | A | 2/1993 | Serwer et al. |
| 5,226,421 | A | 7/1993 | Frisbie et al. |
| 5,250,034 | A | 10/1993 | Appling et al. |
| 5,261,291 | A | 11/1993 | Schoch et al. |
| 5,267,985 | A | 12/1993 | Shimada et al. |
| 5,269,291 | A | 12/1993 | Carter |
| 5,271,406 | A | 12/1993 | Ganguly et al. |
| 5,279,546 | A | 1/1994 | Mische et al. |
| 5,282,785 | A | 2/1994 | Shapland et al. |
| 5,286,254 | A | 2/1994 | Shapland et al. |
| 5,295,484 | A | 3/1994 | Marcus et al. |
| 5,304,115 | A | 4/1994 | Pflueger |
| 5,307,816 | A | 5/1994 | Hashimoto |
| 5,313,949 | A | 5/1994 | Yock |
| 5,315,998 | A | 5/1994 | Tachibana et al. |
| 5,318,014 | A | 6/1994 | Carter |
| 5,323,769 | A | 6/1994 | Bommannan |
| 5,327,891 | A | 7/1994 | Rammler et al. |
| 5,328,470 | A | 7/1994 | Nabel et al. |
| 5,342,292 | A | 8/1994 | Nita et al. |
| 5,344,395 | A | 9/1994 | Whalen et al. |
| 5,344,435 | A | 9/1994 | Turner et al. |
| 5,345,940 | A | 9/1994 | Seward et al. |
| 5,348,481 | A | 9/1994 | Ortiz |
| 5,351,693 | A | 10/1994 | Taimisto et al. |
| 5,353,798 | A | 10/1994 | Sieben |
| 5,354,279 | A | 10/1994 | Hofling |
| 5,362,309 | A | 11/1994 | Carter |
| 5,363,853 | A | 11/1994 | Lieber |
| 5,368,036 | A | 11/1994 | Tamaka et al. |
| 5,368,557 | A | 11/1994 | Nita |
| 5,368,558 | A | 11/1994 | Nita |
| 5,370,675 | A | 12/1994 | Edwards et al. |
| 5,372,138 | A | 12/1994 | Crowley et al. |
| 5,380,273 | A | 1/1995 | Dubrul et al. |
| 5,385,148 | A | 1/1995 | Lesh et al. |
| 5,390,678 | A | 2/1995 | Gesswein et al. |
| 5,397,293 | A | 3/1995 | Alliger et al. |
| 5,399,158 | A | 3/1995 | Lauer et al. |
| 5,401,237 | A | 3/1995 | Tachibana et al. |
| 5,405,322 | A | 4/1995 | Lennox et al. |
| 5,421,338 | A | 6/1995 | Crowley et al. |
| 5,423,797 | A | 6/1995 | Adrian et al. |
| 5,431,663 | A | 7/1995 | Carter |
| 5,440,914 | A | 8/1995 | Tachibana et al. |
| 5,445,155 | A | 8/1995 | Sieben |
| 5,447,509 | A | 9/1995 | Mills et al. |
| 5,447,510 | A | 9/1995 | Jensen |
| 5,453,575 | A | 9/1995 | O'Donnell et al. |
| 5,456,259 | A | 10/1995 | Barlow et al. |
| 5,458,568 | A | 10/1995 | Racchini et al. |
| 5,462,523 | A | 10/1995 | Samson et al. |
| 5,465,726 | A | 11/1995 | Dickinson et al. |
| 5,474,530 | A | 12/1995 | Passafaro et al. |
| 5,474,531 | A * | 12/1995 | Carter .............. 604/22 |
| 5,498,238 | A | 3/1996 | Shapland et al. |
| 5,509,896 | A | 4/1996 | Carter |
| 5,514,092 | A | 5/1996 | Forman et al. |
| 5,520,189 | A | 5/1996 | Malinowski et al. |
| 5,523,058 | A | 6/1996 | Umemura et al. |
| 5,533,986 | A | 7/1996 | Mottola et al. |
| 5,542,917 | A | 8/1996 | Nita et al. |
| 5,542,935 | A | 8/1996 | Unger et al. |
| 5,558,092 | A | 9/1996 | Unger et al. |
| 5,560,362 | A | 10/1996 | Silwa, Jr. et al. |
| 5,569,197 | A | 10/1996 | Helmus et al. |
| 5,582,586 | A | 12/1996 | Tachibana et al. |
| 5,588,432 | A | 12/1996 | Crowley |
| 5,603,327 | A | 2/1997 | Eberle |
| 5,603,694 | A | 2/1997 | Brown et al. |
| 5,606,974 | A | 3/1997 | Castellano et al. |
| 5,617,851 | A | 4/1997 | Lipkovker |
| 5,618,275 | A | 4/1997 | Bock |
| 5,620,409 | A | 4/1997 | Gans et al. |
| 5,624,382 | A | 4/1997 | Oppelt |
| 5,628,730 | A | 5/1997 | Shapland et al. |
| 5,630,837 | A * | 5/1997 | Crowley .............. 601/2 |
| 5,648,098 | A | 7/1997 | Porter |
| 5,656,016 | A | 8/1997 | Ogden et al. |
| 5,660,180 | A | 8/1997 | Malinowski et al. |
| 5,660,909 | A | 8/1997 | Tachibana et al. |
| 5,665,076 | A | 9/1997 | Roth et al. |
| 5,681,296 | A | 10/1997 | Ishida |
| 5,695,460 | A | 12/1997 | Siegel et al. |
| 5,697,897 | A | 12/1997 | Buchholtz et al. |
| 5,713,831 | A | 2/1998 | Olsson |
| 5,713,848 | A | 2/1998 | Dubrul et al. |
| 5,720,710 | A | 2/1998 | Tachibana et al. |
| 5,724,976 | A | 3/1998 | Hirama et al. |
| 5,725,494 | A | 3/1998 | Brisken |
| 5,728,062 | A | 3/1998 | Brisken |
| 5,733,315 | A | 3/1998 | Burdette et al. |
| 5,735,811 | A | 4/1998 | Brisken |
| 5,752,930 | A | 5/1998 | Baudino et al. |
| 5,772,632 | A | 6/1998 | Forman |
| 5,775,338 | A | 7/1998 | Hastings |
| 5,779,673 | A | 7/1998 | Roth et al. |
| 5,807,395 | A | 9/1998 | Mulier et al. |
| 5,817,021 | A | 10/1998 | Reichenberger |
| 5,823,962 | A | 10/1998 | Lerch et al. |
| 5,827,203 | A | 10/1998 | Nita |
| 5,827,313 | A | 10/1998 | Ream |
| 5,834,880 | A | 11/1998 | Lewandowski et al. |
| 5,840,031 | A | 11/1998 | Crowley |
| 5,846,218 | A | 12/1998 | Brisken et al. |
| 5,876,345 | A | 3/1999 | Eaton et al. |
| 5,925,016 | A | 7/1999 | Chornenky et al. |
| 5,928,186 | A | 7/1999 | Homsma et al. |
| 5,935,124 | A | 8/1999 | Klumb et al. |
| 5,938,595 | A | 8/1999 | Glass et al. |
| 5,941,868 | A | 8/1999 | Kaplan et al. |
| 5,957,851 | A | 9/1999 | Hossack |
| 5,957,882 | A | 9/1999 | Nita et al. |
| 5,957,941 | A | 9/1999 | Ream |
| 5,971,949 | A | 10/1999 | Levin et al. |
| 5,976,120 | A | 11/1999 | Chow et al. |
| 5,984,882 | A | 11/1999 | Rosenschein et al. |
| 5,997,497 | A | 12/1999 | Nita et al. |
| 6,004,269 | A | 12/1999 | Crowley et al. |
| 6,024,703 | A | 2/2000 | Zanelli et al. |
| 6,024,718 | A | 2/2000 | Chen et al. |
| 6,027,515 | A | 2/2000 | Cimino |
| 6,033,397 | A | 3/2000 | Laufer et al. |
| 6,053,868 | A | 4/2000 | Geistert et al. |
| 6,059,731 | A | 5/2000 | Seward et al. |

(56) References Cited

U.S. PATENT DOCUMENTS

| | | |
|---|---|---|
| 6,063,069 A | 5/2000 | Cragg et al. |
| 6,066,123 A | 5/2000 | Bednarski et al. |
| 6,078,830 A | 6/2000 | Levin et al. |
| 6,088,613 A | 7/2000 | Unger |
| 6,089,573 A | 7/2000 | Udagawa |
| 6,110,098 A | 8/2000 | Renirie et al. |
| 6,110,314 A | 8/2000 | Nix et al. |
| 6,113,546 A | 9/2000 | Suorsa et al. |
| 6,113,570 A | 9/2000 | Siegel et al. |
| 6,117,101 A | 9/2000 | Diederich et al. |
| 6,120,454 A | 9/2000 | Suorsa et al. |
| 6,135,971 A | 10/2000 | Hutchinson et al. |
| 6,135,976 A | 10/2000 | Tachibana et al. |
| 6,149,599 A | 11/2000 | Schlesinger et al. |
| 6,176,842 B1 | 1/2001 | Tachibana et al. |
| 6,196,973 B1 | 3/2001 | Lazenby et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,283,920 B1 | 9/2001 | Eberle et al. |
| 6,287,271 B1 | 9/2001 | Dubrul et al. |
| 6,296,610 B1 | 10/2001 | Schneider et al. |
| 6,296,619 B1 | 10/2001 | Brisken et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,361,500 B1 | 3/2002 | Masters |
| 6,361,554 B1 | 3/2002 | Brisken |
| 6,366,719 B1 | 4/2002 | Heath et al. |
| 6,372,498 B2 | 4/2002 | Newman et al. |
| 6,379,320 B1 | 4/2002 | Lafon et al. |
| 6,387,052 B1 | 5/2002 | Quinn et al. |
| 6,391,042 B1 | 5/2002 | Cimino |
| 6,398,772 B1 | 6/2002 | Bond et al. |
| 6,416,740 B1 | 7/2002 | Unger |
| 6,423,026 B1 | 7/2002 | Gesswein et al. |
| 6,433,464 B2 | 8/2002 | Jones |
| 6,437,487 B1 | 8/2002 | Mohr, III et al. |
| 6,456,863 B1 | 9/2002 | Levin |
| 6,461,314 B1 | 10/2002 | Pant et al. |
| 6,464,680 B1 | 10/2002 | Brisken et al. |
| 6,471,683 B2 | 10/2002 | Drasler et al. |
| 6,478,765 B2 | 11/2002 | Siegel et al. |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,537,224 B2 | 3/2003 | Mauchamp et al. |
| 6,537,306 B1 | 3/2003 | Burdette et al. |
| 6,542,767 B1 | 4/2003 | McNichols et al. |
| 6,551,337 B1 | 4/2003 | Rabiner et al. |
| 6,558,366 B1 | 5/2003 | Drasler et al. |
| 6,560,837 B1 | 5/2003 | Hodjat et al. |
| 6,561,998 B1 | 5/2003 | Roth et al. |
| 6,562,021 B1 | 5/2003 | Derbin et al. |
| 6,565,552 B1 | 5/2003 | Barbut |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner et al. |
| 6,582,392 B1 | 6/2003 | Bennett et al. |
| 6,585,763 B1 | 7/2003 | Keilman et al. |
| 6,589,182 B1 | 7/2003 | Loftman et al. |
| 6,599,288 B2 | 7/2003 | Maguire et al. |
| 6,605,084 B2 | 8/2003 | Acker et al. |
| 6,607,502 B1 | 8/2003 | Maguire et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,547 B2 | 11/2003 | Rabiner et al. |
| 6,660,013 B2 | 12/2003 | Rabiner |
| 6,663,613 B1 | 12/2003 | Evans et al. |
| 6,676,626 B1 | 1/2004 | Bennett et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,711,953 B2 | 3/2004 | Hayashi et al. |
| 6,723,063 B1 | 4/2004 | Zhang et al. |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,767,345 B2 | 6/2004 | St. Germain et al. |
| 6,758,857 B2 | 7/2004 | Cioanta et al. |
| 6,824,515 B2 | 11/2004 | Suorsa et al. |
| 6,824,575 B1 | 11/2004 | Otomo et al. |
| 6,830,577 B2 | 12/2004 | Nash et al. |
| 6,849,062 B2 | 2/2005 | Kantor |
| 6,855,123 B2 | 2/2005 | Nita |
| 6,866,670 B2 | 3/2005 | Rabiner et al. |
| 6,905,505 B2 | 6/2005 | Dodson, Jr. et al |
| 6,921,371 B2 | 7/2005 | Wilson |
| 6,929,633 B2 | 8/2005 | Evans et al. |
| 6,942,620 B2 | 9/2005 | Nita et al. |
| 6,945,937 B2 | 9/2005 | Culp et al. |
| 6,979,293 B2 | 12/2005 | Hansmann et al. |
| 6,985,771 B2 | 1/2006 | Fischell et al. |
| 7,077,820 B1 | 7/2006 | Kadziauskas et al. |
| 7,089,063 B2 | 8/2006 | Lesh et al. |
| 7,137,963 B2 | 11/2006 | Nita |
| 7,141,044 B2 | 11/2006 | Gentsler |
| 7,166,098 B1 | 1/2007 | Steward et al. |
| 7,186,246 B2 | 3/2007 | Bennett et al. |
| 7,220,233 B2 | 5/2007 | Nita |
| 7,220,239 B2 | 5/2007 | Wilson et al. |
| 7,309,334 B2 | 12/2007 | von Hoffmann |
| 7,335,180 B2 | 2/2008 | Nita |
| 7,341,569 B2 | 3/2008 | Soltani et al. |
| 7,503,895 B2 | 3/2009 | Rabiner et al. |
| 7,540,852 B2 | 6/2009 | Nita |
| 7,567,016 B2 | 7/2009 | Lu et al. |
| 7,604,608 B2 | 10/2009 | Nita |
| 7,621,902 B2 | 11/2009 | Nita et al. |
| 7,758,509 B2 | 7/2010 | Angelsen et al. |
| 7,771,372 B2 | 8/2010 | Wilson |
| 7,789,830 B2 | 9/2010 | Fujita et al. |
| 7,828,754 B2 | 11/2010 | Abe et al. |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita |
| 8,167,831 B2 | 5/2012 | Wilson et al. |
| 2001/0000791 A1 | 5/2001 | Suorsa et al. |
| 2001/0007861 A1 | 7/2001 | Newman et al. |
| 2001/0007940 A1 | 7/2001 | Tu et al. |
| 2001/0025190 A1 | 9/2001 | Weber et al. |
| 2001/0037106 A1 | 11/2001 | Shadduck et al. |
| 2001/0039419 A1 | 11/2001 | Francischelli et al. |
| 2001/0041842 A1 | 11/2001 | Eberie et al. |
| 2001/0041880 A1 | 11/2001 | Brisken et al. |
| 2002/0000763 A1 | 1/2002 | Jones |
| 2002/0019644 A1 | 2/2002 | Hastings et al. |
| 2002/0032394 A1 | 3/2002 | Brisken et al. |
| 2002/0045890 A1 | 4/2002 | Celliers et al. |
| 2002/0052620 A1 | 5/2002 | Barbut |
| 2002/0068869 A1 | 6/2002 | Brisken et al. |
| 2002/0077550 A1 | 6/2002 | Rabiner et al. |
| 2002/0082238 A1 | 6/2002 | Newman et al. |
| 2002/0087083 A1 | 7/2002 | Nix et al. |
| 2002/0099292 A1 | 7/2002 | Brisken et al. |
| 2002/0123787 A1 | 9/2002 | Weiss |

(56) References Cited

U.S. PATENT DOCUMENTS

| | | |
|---|---|---|
| 2002/0133111 A1 | 9/2002 | Shadduck et al. |
| 2002/0188276 A1 | 12/2002 | Evans et al. |
| 2002/0193708 A1 | 12/2002 | Thompson et al. |
| 2003/0036705 A1 | 2/2003 | Hare et al. |
| 2003/0040501 A1 | 2/2003 | Newman et al. |
| 2003/0050662 A1 | 3/2003 | Michael |
| 2003/0065263 A1 | 4/2003 | Hare et al. |
| 2003/0069525 A1 | 4/2003 | Brisken et al. |
| 2003/0109812 A1 | 6/2003 | Corl et al. |
| 2003/0135262 A1 | 7/2003 | Dretler et al. |
| 2003/0163147 A1 | 8/2003 | Hare et al. |
| 2003/0220568 A1 | 11/2003 | Hansmann et al. |
| 2003/0236539 A1 | 12/2003 | Rabiner et al. |
| 2004/0001809 A1 | 1/2004 | Brisken et al. |
| 2004/0019318 A1 | 1/2004 | Wilson et al. |
| 2004/0024347 A1 | 2/2004 | Wilson et al. |
| 2004/0024393 A1 | 2/2004 | Nita |
| 2004/0039311 A1 | 2/2004 | Nita et al. |
| 2004/0049148 A1 | 3/2004 | Rodriguez et al. |
| 2004/0059313 A1 | 3/2004 | Anderson et al. |
| 2004/0068189 A1 | 4/2004 | Wilson et al. |
| 2004/0097996 A1 | 5/2004 | Hare et al. |
| 2004/0138570 A1 | 7/2004 | Nita et al. |
| 2004/0162571 A1 | 8/2004 | Rabiner et al. |
| 2004/0171981 A1 | 9/2004 | Buffen et al. |
| 2004/0220514 A1 | 11/2004 | Cafferata |
| 2004/0236350 A1 | 11/2004 | Bolduc et al. |
| 2004/0243062 A1 | 12/2004 | Henry |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043629 A1 | 2/2005 | Rabiner et al. |
| 2005/0043753 A1 | 2/2005 | Rabiner et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0192556 A1 | 9/2005 | Soltani et al. |
| 2005/0192558 A1 | 9/2005 | Bernard et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Mun Hong |
| 2005/0256410 A1 | 11/2005 | Rabiner et al. |
| 2005/0288695 A1 | 12/2005 | Jenson et al. |
| 2006/0069303 A1 | 3/2006 | Couvillon |
| 2006/0106308 A1 | 5/2006 | Hansmann et al. |
| 2006/0116610 A1 | 6/2006 | Hare et al. |
| 2006/0173387 A1 | 8/2006 | Hansmann et al. |
| 2006/0184070 A1 | 8/2006 | Hansmann et al. |
| 2007/0037119 A1 | 2/2007 | Pal et al. |
| 2007/0066978 A1 | 3/2007 | Schafer et al. |
| 2007/0225619 A1 | 9/2007 | Rabiner et al. |
| 2007/0239027 A1 | 10/2007 | Nita |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 9/2008 | Abrahamson et al. |
| 2008/0306499 A1 | 12/2008 | Katoh et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0112150 A1 | 4/2009 | Unger et al. |
| 2009/0216246 A1 | 8/2009 | Nita et al. |
| 2010/0010393 A1 | 1/2010 | Duffy et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2011/0160621 A1 | 6/2011 | Nita |
| 2011/0201974 A1 | 8/2011 | Hansmann et al. |
| 2011/0288449 A1 | 11/2011 | Schenkengel |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Nita |
| 2012/0179073 A1 | 7/2012 | Nita |
| 2012/0197277 A1 | 8/2012 | Stinis |

FOREIGN PATENT DOCUMENTS

| | | |
|---|---|---|
| EP | 0 629 382 | 12/1994 |
| EP | 0744189 | 11/1996 |
| EP | 1090658 | 4/2001 |
| EP | 0 746 245 | 11/2002 |
| JP | 52115591 | 9/1977 |
| JP | 2180275 | 7/1990 |
| WO | WO 89/04142 | 5/1989 |
| WO | WO 92/00113 | 1/1992 |
| WO | WO 95/01751 | 1/1995 |
| WO | WO 95/05866 | 3/1995 |
| WO | WO 95/26777 | 10/1995 |
| WO | WO 96/04955 | 2/1996 |
| WO | WO 96/27341 | 9/1996 |
| WO | WO 96/29935 | 10/1996 |
| WO | WO 96/36286 | 11/1996 |
| WO | WO 97/19645 | 5/1997 |
| WO | WO 98/11826 | 3/1998 |
| WO | WO 98/018391 | 5/1998 |
| WO | WO 98/048711 | 11/1998 |
| WO | WO 98/56462 | 12/1998 |
| WO | WO 99/32184 | 7/1999 |
| WO | WO 99/33500 | 7/1999 |
| WO | WO 99/33550 | 7/1999 |
| WO | WO 99/34858 | 7/1999 |
| WO | WO 99/39647 | 8/1999 |
| WO | WO 99/44512 | 9/1999 |
| WO | WO 00/00095 A | 1/2000 |
| WO | WO 00/38580 | 7/2000 |
| WO | WO 00/69341 | 11/2000 |
| WO | WO 01/54754 A1 | 8/2001 |
| WO | WO 01/87174 A1 | 11/2001 |
| WO | WO 01/095788 | 12/2001 |
| WO | WO 02/13678 | 2/2002 |
| WO | WO 02/15803 | 2/2002 |
| WO | WO 02/15804 | 2/2002 |
| WO | WO 03/051208 | 6/2003 |
| WO | WO 2005/027756 | 3/2005 |
| WO | WO 2005/084552 | 9/2005 |
| WO | WO 2005/084553 | 9/2005 |

OTHER PUBLICATIONS

Lee et al., "Arrays of Multielement Ultrasound Applicators for Interstitial Hyperthermia"; IEEE Transactions on Biomedical Engineering; vol. 46, No. 7; Jul. 1999.

Schafer et al., "Influence of Ultrasound Operating Parameters on Ultrasound Induced Thrombolysis in Vitro"; Ultrasound in Med. & Biol., vol. 23, No. 6, pp. 841-847.

Tsetis et al., "Potential Benefits From Heating the High-Dose Rtpa Boluses Used in Catheter-Directed Thrombolysis for Acute/Subacute Lower Limb Ischemia", J Endovasc. Ther. 10:739-744 (2003).

* cited by examiner

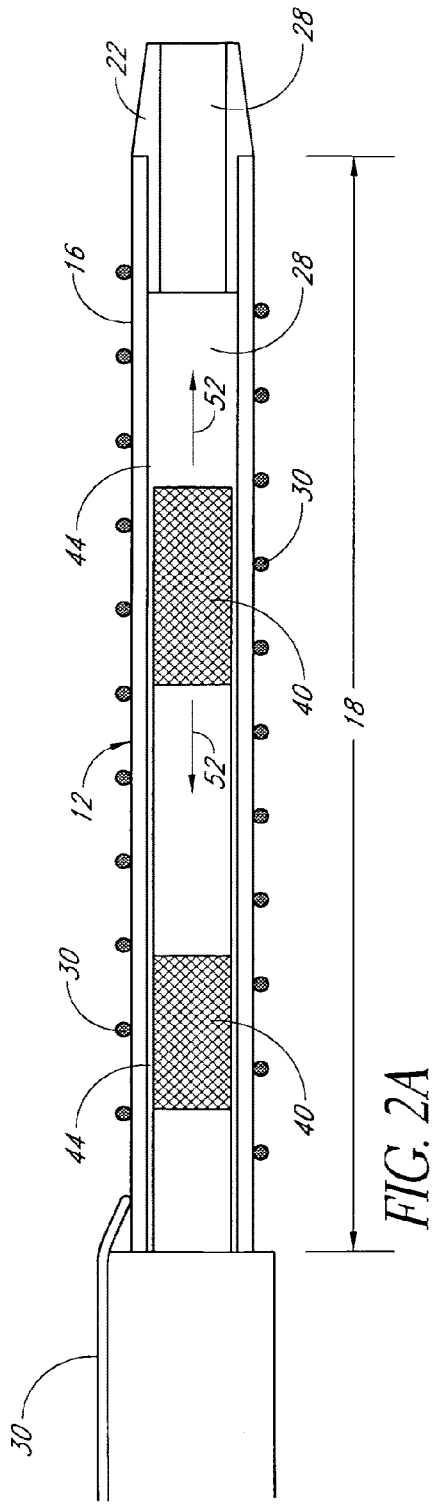
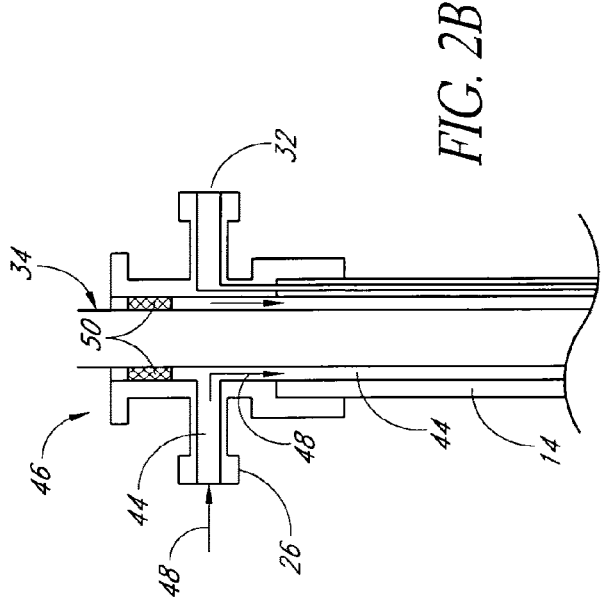

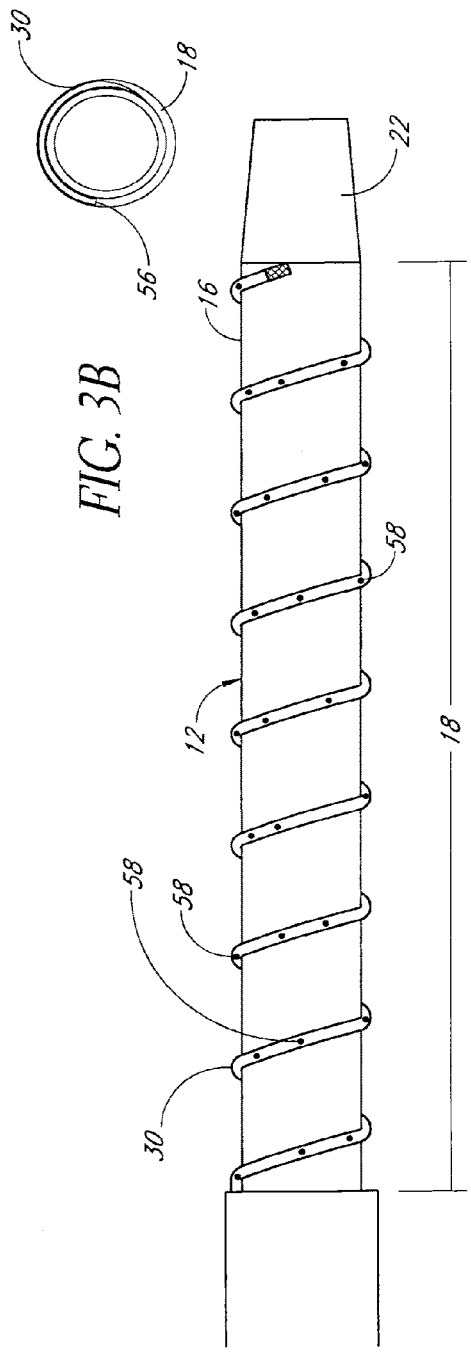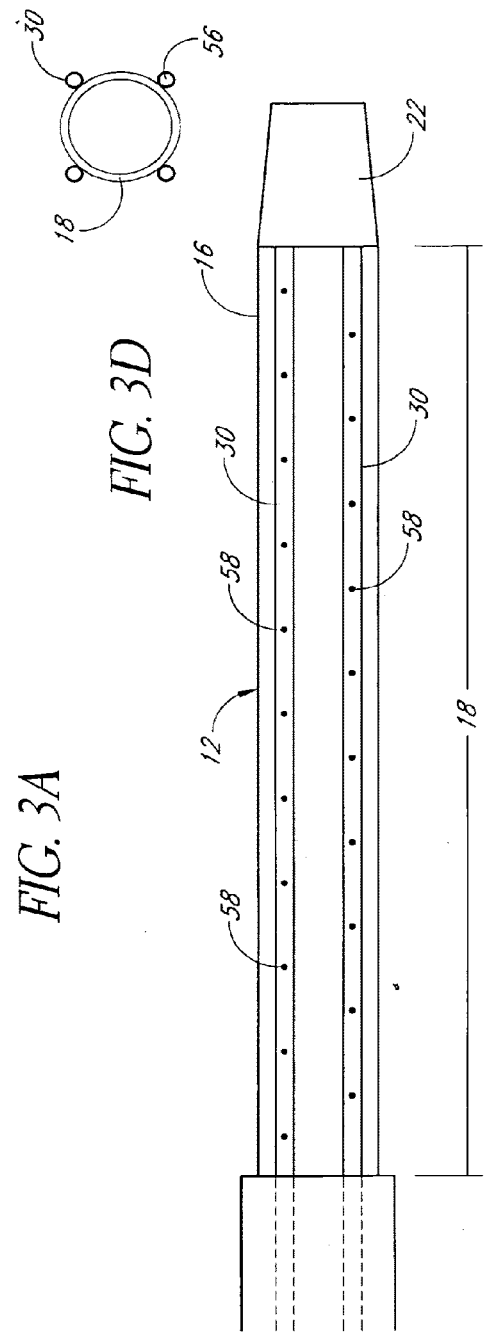

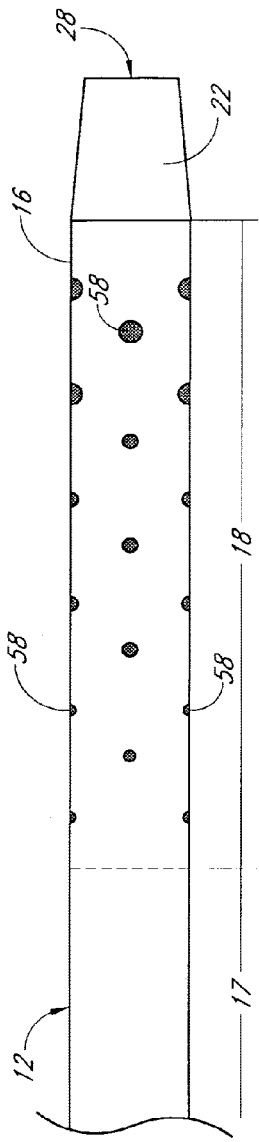
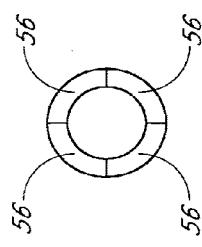
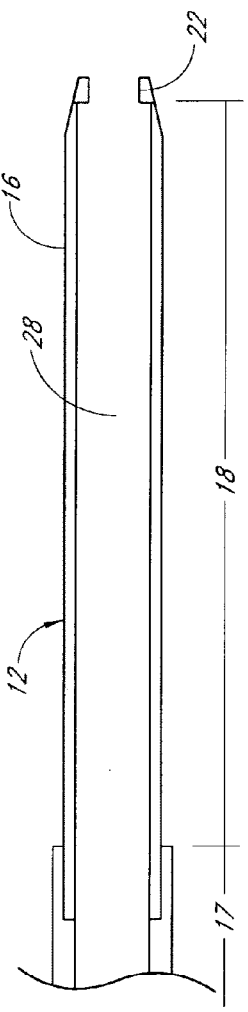
FIG. 4A
FIG. 4B
FIG. 5

SHEATH FOR USE WITH AN ULTRASOUND ELEMENT

PRIORITY APPLICATIONS

This application is a continuation of U.S. patent application Ser. No. 11/418,491, filed May 3, 2006, now abandoned, which is a continuation of U.S. patent application Ser. No. 10/369,270, filed Feb. 18, 2003, now U.S. Pat. No. 7,413,556, which is a continuation of U.S. patent application Ser. No. 09/107,078, filed Jun. 29, 1998, now U.S. Pat. No. 6,723,063. The entire disclosure of these priority applications is hereby incorporated by reference herein.

BACKGROUND OF THE INVENTION

1. Field of the Invention

The present invention relates to an ultrasound enhanced drug delivery apparatus, and more particularly, to an ultrasound element which can be movably positioned within a drug delivery sheath.

2. Description of the Related Art

Thrombus formation is a protective and healing mechanism, however, formation of thrombi can be detrimental. For instance, if a blood vessel becomes blocked, distal tissue may be deprived of oxygen with resulting damage or necrosis. In the case of cerebral circulation, an arterial thrombus blockage is one cause of cerebral strokes. In the case of coronary thrombosis, blockage and subsequent distal tissue necrosis of cardiac muscle tissue will impair cardiac pump output, may cause electrical abnormalities, and potentially catastrophic heart failure and death. The thrombus can form at the site of artery narrowing due to arterial wall damage or disease, or the thrombus may have broken free from some proximal site only to become wedged in a distal stenosis. Thrombus can also form subsequent to attempts to remove a stenosis using balloon angioplasty or rotary atherectomy.

Ultrasound sheaths have been described specifically for removal or dissolution of thrombus (U.S. Patents: Tachibana U.S. Pat. No. 5,197,946; Bernstein U.S. Pat. No. 5,163,421; Weng U.S. Pat. No. 5,269,297). The sheaths of Bernstein and Weng place an ultrasound generator external to the body and transmit acoustic energy through a metal wire wave-guide to the distal sheath. The sheath of Tachibana includes a small ultrasound element positioned at the distal end of the sheath that is energized by electrical wires. In either case, ultrasound energy is delivered to and radiated from the distal tip of the sheath in the vicinity of a blocking thrombus. The application of ultrasound can directly emulsify nearby thrombus through the motion of the sheath tip, associated cavitation, and bioeffects.

The application of ultrasound can also enhance delivery of drug into a vessel wall. There are instances where the vessel wall is diseased or has been injured during balloon angioplasty or rotary atherectomy. Narrowing of the vessel can occur in response to these injuries. Certain drugs, such as heparin, may inhibit this narrowing of the blood vessel if the drug can be delivered into the blood vessel wall. A sheath can be used to deliver drugs into any portion of the body or target organ. Ultrasound energy in the presence of these drugs can enhance the delivery through and across bodily fluids and tissue. Hence, an ultrasound drug delivery sheath placed in a blood vessel will assist delivery across the blood vessel Wall, whether it be an artery or a vein, into the surrounding muscle or tissue.

The intensity of the ultrasound delivered from a cylindrical ultrasound element decreases exponentially with radial distance from the sheath tip. Hence, treatment of thrombi is limited to the circumferential area surrounding of the sheath tip of a sheath with an ultrasound element. This limited treatment area may be effective for small length clots, however, larger clots must be treated one section at a time.

Some thrombi can be large. For instance, a deep vein thrombus in a patient's lower leg and can have a length from several centimeters to as much as 30-50 cm long. Early treatment protocols for these long thrombi used a drug infusion sheath to drip lytic drug at one end of a thrombus. As the thrombus was dissolved, the sheath would be advanced. This process was repeated until the entire clot was dissolved. More current therapy for a deep vein thrombosis is to use an infusion sheath with drug infusion ports distributed along the lateral dimension of the sheath. The sheath can be pushed through the entire length of the clot. The thrombolytic drug is then infused throughout the lesion for a period of hours.

There is a need for an ultrasound sheath that is useful for treating a deep vein thrombus to enhance and accelerate the action of the thrombolytic drug. There is a further need for an ultrasound sheath that is useful for treating vessel lesions, particularly those that have extensive lengths.

SUMMARY OF THE INVENTION

A system for delivering ultrasound energy to a treatment section in a vessel is disclosed. The system includes a sheath with a utility lumen and an energy delivery section at least partially constructed from a material which transmits ultrasound energy. The system also includes a drug delivery member having a plurality of drug delivery ports which are positioned adjacent the energy delivery section. The system further includes an elongated body including at least one ultrasound element and configured to be movably positioned within the utility lumen to transmit the ultrasound energy from the ultrasound element through the energy delivery section.

In another embodiment the system includes a sheath having a utility lumen configured to movably receive an elongated body with an ultrasound element and an energy delivery section at least partially constructed from a material which transmits ultrasound energy from the ultrasound element. The system also includes a drug delivery member having a plurality of drug delivery ports which are configured to be positioned adjacent the energy delivery section.

A sheath for delivering ultrasound energy to a treatment section in a vessel is also disclosed. The sheath includes a utility lumen configured to movably receive an elongated body with an ultrasound element. The sheath also includes an energy delivery section at least partially constructed from a material which transmits ultrasound energy from the ultrasound element. A plurality, of drug delivery ports are positioned adjacent the energy delivery section.

In another embodiment, the sheath includes a utility lumen configured to movably receive an elongated body with an ultrasound element. The sheath also includes an energy delivery section, at least partially constructed from a material which transmits ultrasound energy from the ultrasound element. At least one temperature sensor is positioned adjacent the energy delivery section.

A system for delivering ultrasound energy to a treatment section in a vessel is disclosed. The system includes a sheath having a utility lumen and an energy delivery section which is at least partially constructed from a material which transmits ultrasound energy. An expandable balloon positioned at least partially adjacent the energy delivery section. The system also includes an elongated body with at least one ultrasound element. The elongated body is configured to be movably positioned within the utility lumen to transmit the ultrasound energy from the ultrasound element through the energy delivery section.

BRIEF DESCRIPTION OF THE DRAWINGS

FIG. 2A is a cross section of a sheath with an elongated body positioned within a utility lumen.

FIG. 2B is a cross section of a sheath proximal end.

FIG. 3A is a sideview of a sheath distal end.

FIG. 3B is a cross sectional view of a sheath distal end.

FIG. 3C is a sideview of a sheath distal end.

FIG. 3D is a cross sectional view of a sheath distal end.

FIG. 4A is a sideview of a sheath distal end with drug delivery ports of increasing size.

FIG. 4B is a cross sectional view of a sheath distal end.

FIG. 5 is a cross section of a sheath distal end with an integral occlusion device.

DETAILED DESCRIPTION OF THE PREFERRED EMBODIMENT

Figure 1A:
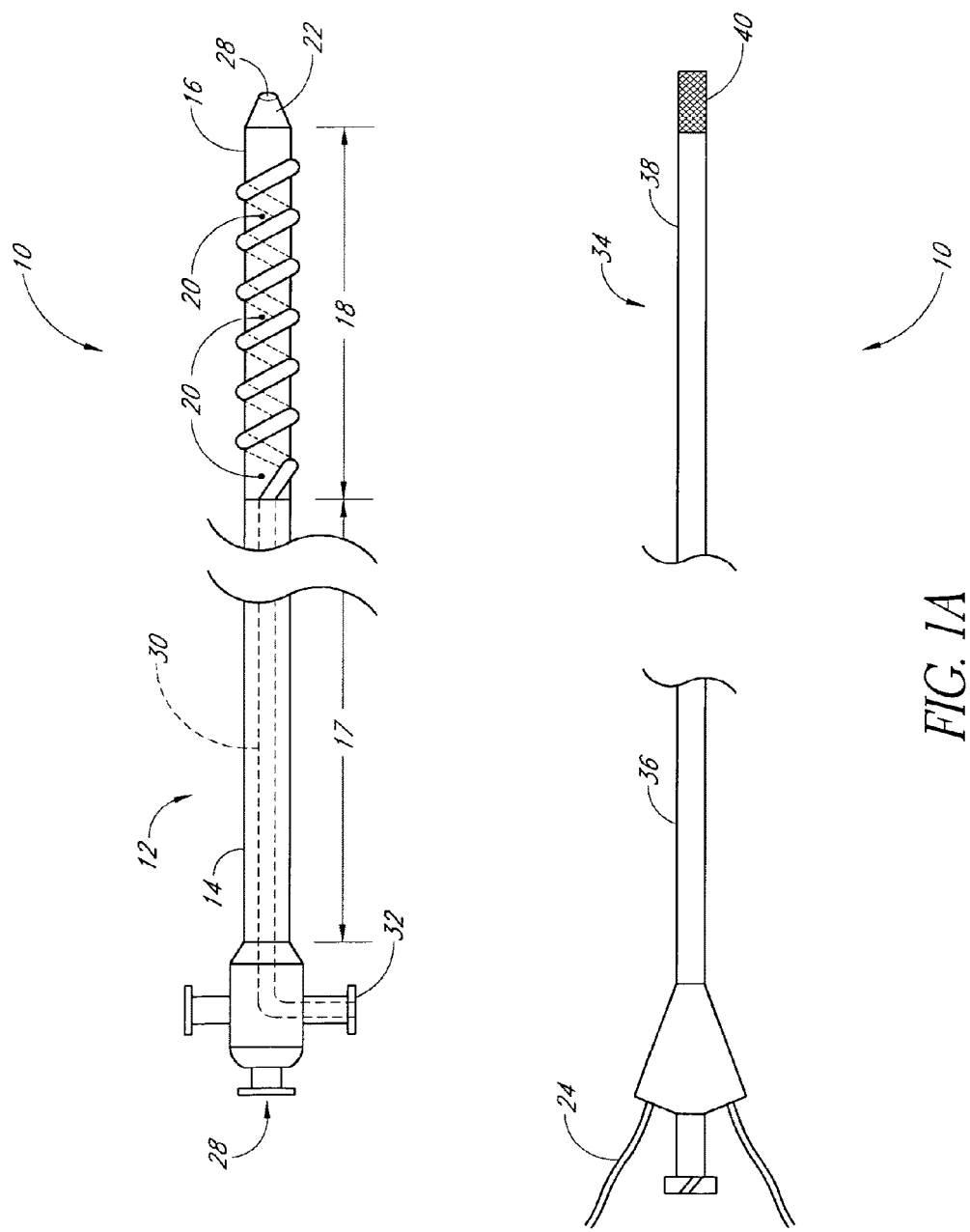
FIG. 1A is a sideview of a sheath and elongated body according to the present invention.

The invention relates to a system for delivering ultrasound energy to a treatment section in a vessel. The system includes a sheath with an energy delivery section at least partially constructed from a material which transmits ultrasound energy. The sheath is designed to be positioned within a vessel such that at least a portion of the energy delivery section is positioned adjacent a treatment site within the vessel. The system also includes an elongated body with an ultrasound element positioned at its distal end. The elongated body can be received in a utility lumen included in the sheath such that the ultrasound element is positioned within the energy delivery section.

Ultrasound energy can be delivered from the ultrasound element through the energy delivery section to the treatment site.

The elongated body can be moved within the utility lumen so the ultrasound element can be moved relative to the energy delivery section. As a result, the ultrasound element can be moved within the treatment site to deliver ultrasound energy to different sections of the treatment site. The motion of the ultrasound element relative to the treatment site can help emulsify a clot, thrombus or other blockage at the treatment site. Since, the ultrasound element is being moved relative to the treatment site within the sheath, the movement of the ultrasound element relative to the treatment site does not damage the vessel including the treatment site.

The elongated body can include a cooling fluid lumen which passes adjacent the ultrasound element. Similarly, a cooling fluid lumen can be formed between the elongated body and the sheath. A cooling fluid can be passed through the cooling fluid lumen to cool the ultrasound element. The heating of the ultrasound element can limit the amount of power which can be provided to the ultrasound element. Cooling the ultrasound element during its operation allows the power provided to the ultrasound element to be increased. As a result, cooling the ultrasound element can increase the efficiency of the treatment. Movement of the ultrasound element can be accomplished manually or through use of an automated method.

The system can also include a drug delivery member which includes a plurality of drug delivery ports which are positioned adjacent to the energy delivery section. The drug delivery ports permit delivery of a drug solution to the treatment site. Ultrasound energy can also be delivered to the treatment site to enhance the effect of the drug within tile treatment site.

The drug delivery member can be external to the energy delivery section. As a result, a drug solution does not need to be delivered through the energy delivery section allowing the energy delivery section to be constructed of acoustically transparent materials which cannot be easily extruded. The energy delivery section can also be very thin since a drug delivery lumen need not pass through materials comprising the energy delivery section. Thinner materials increase the acoustic transparency of the energy delivery section. Suitable materials for the energy delivery section include, but are not limited to, polyimides. The portion of the sheath which is not included in the energy delivery section can be constructed from materials such as polyurethanes, copolyesters, or thermoplastic elastomers which provides the sheath with kink resistance, rigidity and structural support necessary to transport the energy delivery section to the treatment site.

The sheath can also include at least one temperature sensor positioned adjacent the energy delivery section. The temperature sensors can be coupled with a feedback control system. The feedback control system can be used to adjust the level of power delivered to the ultrasound element in response to the signal from at least one temperature sensor. As a result, the temperature at the treatment site can be maintained within a desired range during the treatment.

Figure 1B:
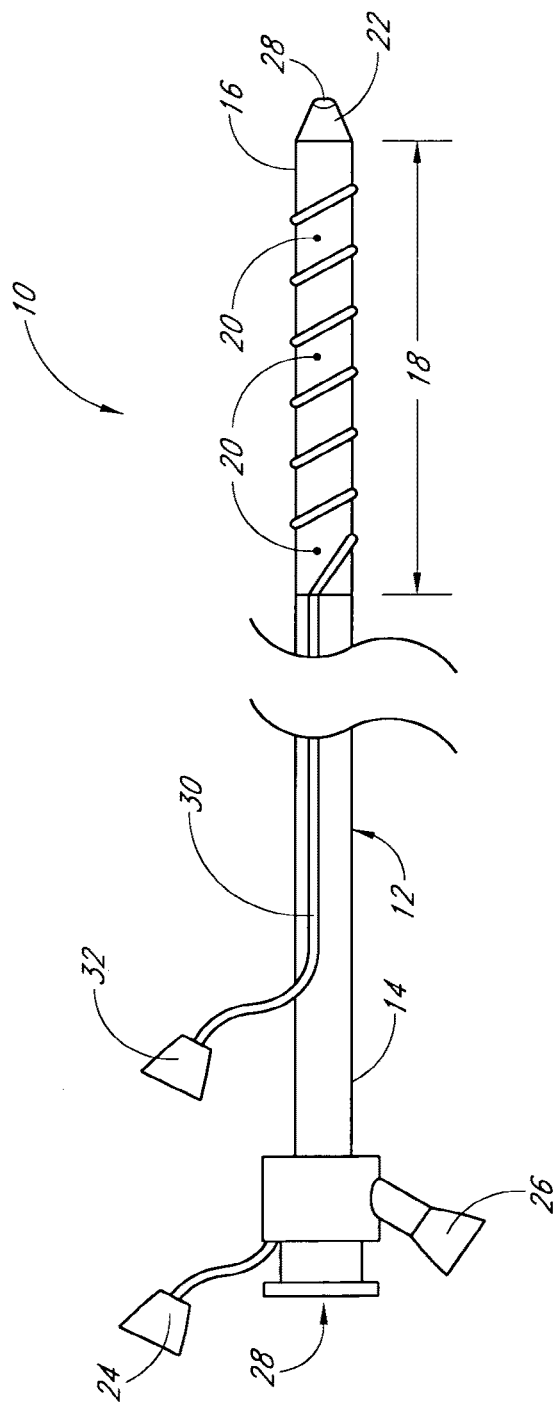
FIG. 1B is a sideview of a sheath and elongated body according to the present invention.

FIG. 1A illustrates a drug delivery system 10 according to the present invention. The system 10 includes a sheath 12 with a sheath proximal end 14 and a sheath distal end 16. The sheath distal end 16 includes, a support section 17, an energy delivery section 18, temperature sensors 20 and an occlusion device 22. The sheath proximal end 14 includes temperature sensor leads 24 and a cooling fluid fitting 26. A utility lumen 28 extends through the sheath 12 along the length of the sheath 12. A drug delivery member 30 is positioned adjacent the energy delivery section. The drug delivery member 30 includes a drug inlet port 32 which can be coupled with a drug source via a connector such as a Luer type fitting. The drug delivery member 30 can be incorporated into the support section 17 as illustrated in FIG. 1A or can external to the support section as illustrated in FIG. 1B. The system 10 also includes an elongated body 34 with a body proximal end 36 and a body distal end 38. An ultrasound element 40 is positioned at the body distal end 38.

The elongated body 34 has an outer diameter which permits the elongated body 34 to be inserted into the utility lumen 28. FIG. 2A illustrates the elongated body 34 threaded through the utility lumen 28 until the ultrasound element 40 is positioned within the energy delivery section 18. Suitable outer diameters of the elongated body 34 include, but are not limited to, 0.010"-0.100". Suitable diameters of the utility lumen 28 include, but are not limited to 0.015"-0.110". The utility lumen 28 extends through the occlusion device 22. The portion of the utility lumen 28 extending through the occlusion device 22 has a diameter which can accommodate a guidewire (not shown) but which prevents the ultrasound element 40 from passing through the occlusion device 22. Suitable inner diameters for the occlusion device 22 include, but are not limited to 0.005"-0.050".

The ultrasound element 40 can be rotated or moved within the energy delivery section 18 as illustrated by the arrows 52 illustrated in FIG. 2A. The movement of the ultrasound element 40 within the energy delivery section 18 can be caused by manipulating the body proximal section while holding the sheath proximal section stationary. The elongated body 34 can be at least partially constructed from a material which provides enough structural support to permit movement of the elongated body 34 within the sheath 12 without kinking of the elongated body 34. Suitable materials for the elongated body 34 include, but are not limited to polyesters, polyurethanes, thermoplastic, elastomers.

As illustrated in FIG. 2A, the outer diameter of the elongated body 34 can be smaller than the diameter of the utility lumen 28 to create a cooling fluid lumen 44 between the elongated body 34 and the utility lumen 28. A cooling fluid can be flowed through the cooling fluid lumen 44, past the ultrasound element 40 and through the occlusion device 22. The flow rate of the cooling fluid and/or the power to the ultrasound element 40 can be adjusted to maintain the temperature of the ultrasound element 40 within a desired range.

Figure 2C:
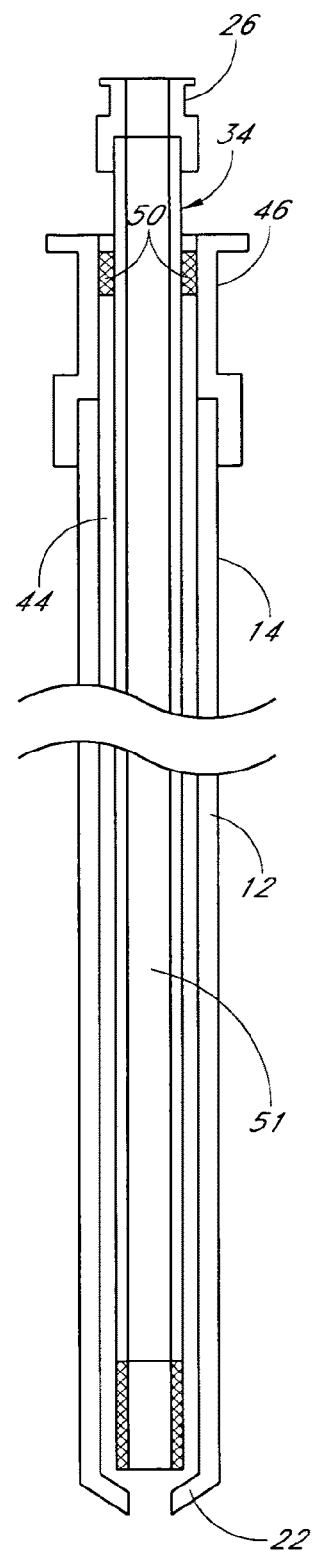
FIG. 2C is a cross section of an elongated body including a body lumen.

The sheath proximal end 14 can include a cap 46 as illustrated in FIG. 2B. A cooling fluid can be flowed from the cooling fluid fitting 26 through the cooling fluid lumen 44 as illustrated by the arrows 48. The cap 46 includes a hemostasis valve 50 with an inner diameter which substantially matches the diameter of the elongated body 34. The matched diameters reduces leaking of the cooling fluid between the cap 46 and the elongated body 34. As illustrated in FIG. 2C, the ultrasound element 40 can be a hollow cylinder and the elongated body can include a body lumen 51 which extends through the ultrasound element 40. The cooling fluid can be flowed through the body lumen past the ultrasound element 40 to provide cooling to the ultrasound element 40.

Figure 2D:
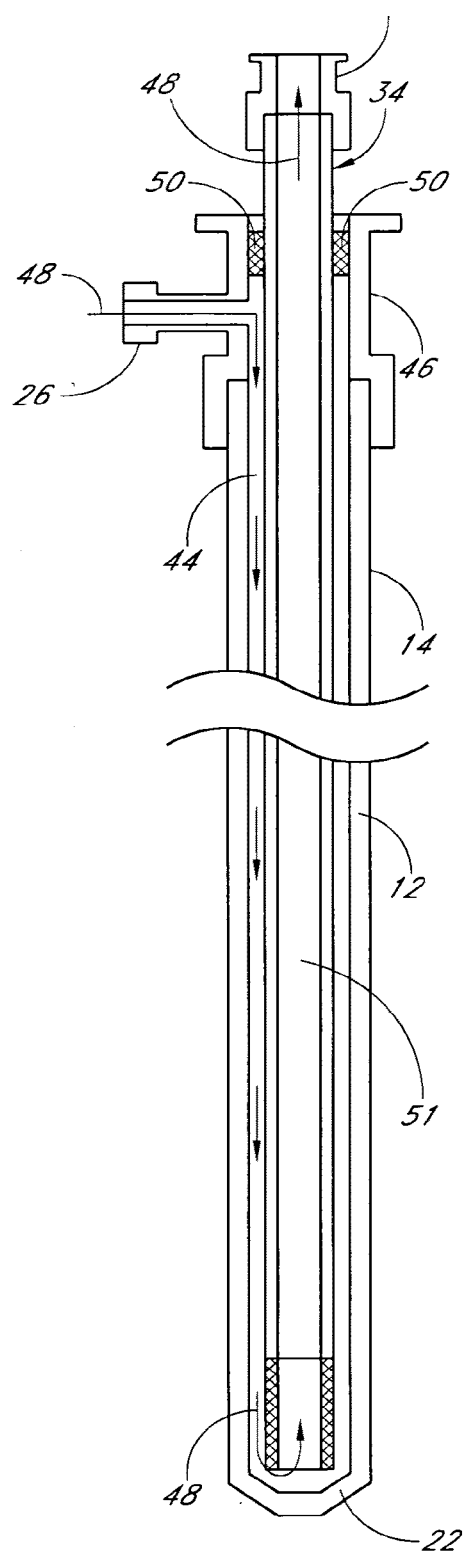
FIG. 2D is a cross section of an elongated body including a body lumen positioned within a sheath including a closed occlusion device.
Figure 2E:
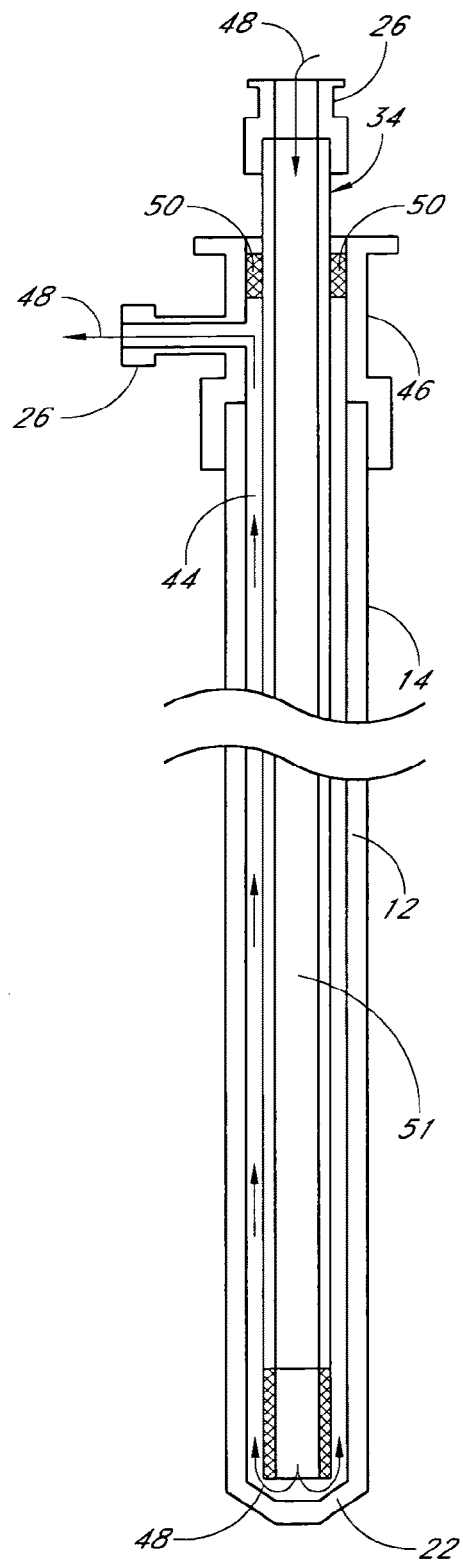
FIG. 2E is a cross section of an elongated body including a body lumen positioned within a sheath including a closed occlusion device.

As illustrated in FIG. 2D, the occlusion device 22 can be integral with the sheath 12 and can have a closed end. The body lumen 51 can serve as a return lumen for the cooling fluid. As a result, the inside and the outside of the ultrasound element 40 are exposed to the cooling fluid to accelerate the cooling of the ultrasound element 40. As illustrated in FIG. 2O, the flow of the cooling fluid can be reversed so the cooling lumen serves as the return cooling fluid lumen. The above cooling schemes permit the power provided to the ultrasound element to be increased in proportion to the cooling flow rate. Further, certain schemes can prevent exposure of the body to cooling fluids.

The drug delivery member 30 includes a drug delivery portion which is positioned adjacent the energy delivery section 18 as illustrated in FIG. 3A. As illustrated in FIG. 3B, the drug delivery member 30 includes a drug delivery lumen 56 extending through the length of the drug delivery member 30.

The drug delivery member 30 also it includes a series of drug delivery ports 58 coupled with the drug delivery lumen 56. A drug source coupled with the drug inlet port 32 can provide a pressure which drives a drug solution through the drug delivery lumen 56 and out the drug delivery ports 58. A suitable material for the drug delivery member 30 includes, but is not limited to, polyimide, polyolefin, polyester.

The sheath 12 can include a plurality of drug delivery members 30. The drug delivery members 30 can be wound around the energy delivery section 18 or they can be positioned along the length of the energy delivery section 18 as illustrated in FIG. 3C. Each drug delivery member 30 can be coupled with the same drug inlet port 32. In another embodiment, each drug delivery member 30 is coupled with independent drug inlet ports 32 so different drug solutions can be, delivered to different drug delivery ports 58.

The drug delivery ports 58 are positioned close enough to achieve a substantially even flow of drug solution around the circumference of the energy delivery section 18 and along the length of the energy delivery sections 18. The proximity of adjacent drug delivery ports 58 can be changed by changing the density of drug delivery ports 58 along the drug delivery member, by changing the number of windings of the drug delivery member around the energy delivery section 18 or by changing the number of drug delivery members 30 included adjacent the energy delivery section 18. A suitable displacements between adjacent drug delivery ports 58 include, but are not limited to, from 0.1" to 1.0", preferable 0.2" to 0.6".

The size of the drug delivery ports 58 can be the same or change along the length of the drug delivery member. For instance, the size of the drug delivery ports 58 distally positioned on the drug delivery section can be larger than the size of the drug delivery ports 58 which are proximally positioned on the drug delivery section. The increase in sizes of the drug delivery ports 58 can be designed to produce similar flowrates of drug solution through each drug delivery port 58. This similar flowrate increases the uniformity of drug solution flowrate along the length of the sheath 12. When the drug delivery ports 58 have similar sizes along the length of the drug delivery member, a suitable size for a drug delivery port 58 includes, but is not limited to 0.0005" to 0.0050". When the size of the drug delivery ports 58 changes along the length of the drug delivery member, suitable sizes for proximally positioned drug delivery ports 58 includes, but is not limited to from 0.0001" to 0.005" and suitable sizes for distally positioned drug delivery ports 58 includes, but is not limited to 0.0005" to 0.0020". The increase in size between adjacent drug delivery ports can be substantially uniform between or along the drug delivery member. The dimensional increase of the drug delivery ports is dependent upon material and diameter of the drug delivery member. The drug delivery ports 58 can be burnt into the drug delivery member 30 with a laser.

Uniformity of the drug solution flow along the length of the sheath 12 can also be increased by increasing the density of the drug delivery ports 58 toward the distal end of the drug delivery member.

Figure 3E:
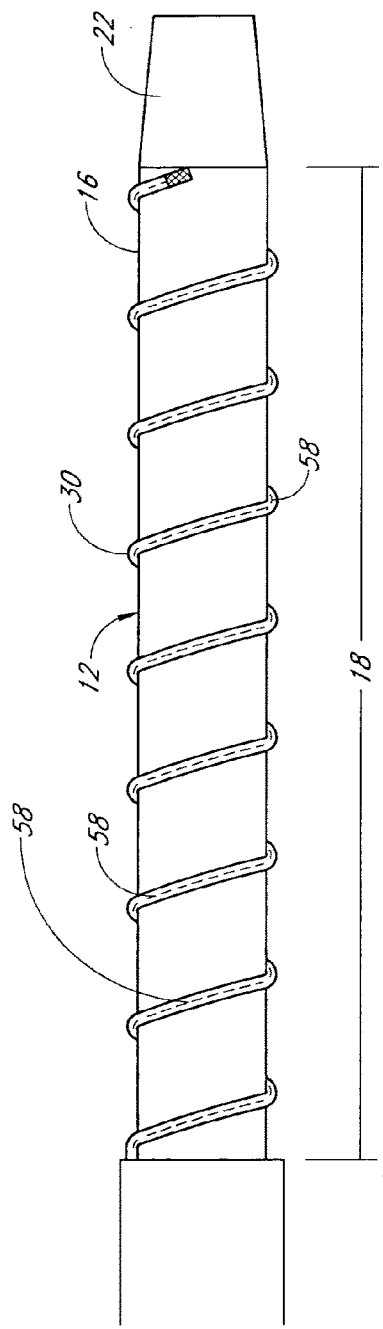
FIG. 3E illustrates a drug delivery member with slit shaped drug delivery ports.
Figure 3F:
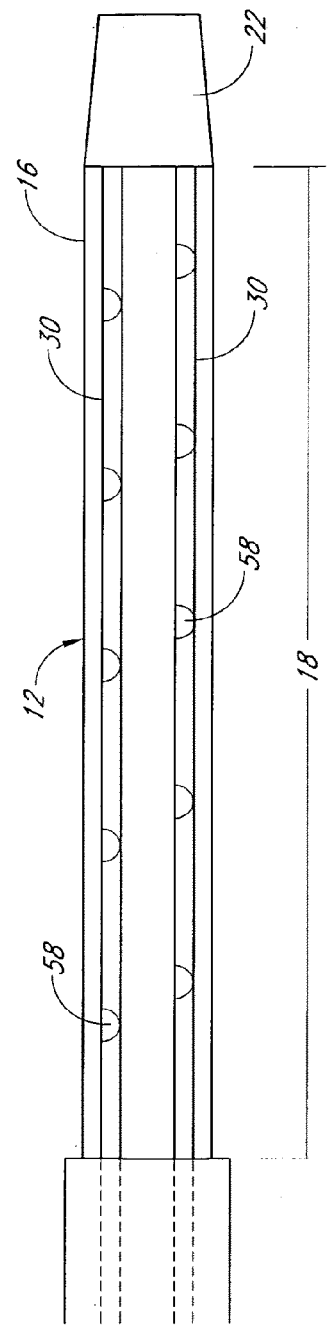
FIG. 3F illustrates a drug delivery member with arc shaped slits as drug delivery ports.

The drug delivery ports 58 can be slits with a straight shape as illustrated in FIG. 3E or an arcuate shape as illustrated in FIG. 3F. The drug delivery member 30 can be constructed from materials such as polyimide, nylon, pebax, polyurethane or silicon. When the drug delivery lumen 56 is filled with drug solution, the slits remain closed until the pressure within the drug delivery lumen exceeds a threshold pressure. As the pressure within the drug delivery lumen builds, the pressure on each of the slits will be approximately uniform. Once, the threshold pressure is reached, the uniform pressure will result in the slits opening almost simultaneously and cause a nearly uniform flow of drug solution out of all the slits. When the pressure within the drug delivery lumen 56 falls below the threshold pressure, the slits close and prevent delivery of additional drug solution. The stiffer the material used to construct the drug deliver member, the higher the threshold pressure required to open the slit shaped drug delivery ports. The slit shape can also prevent the drug delivery ports 58 from opening when exposed to low pressures from outside the sheath 12. As a result, slit shaped drug delivery ports can maximize control of drug delivery.

The sheath 12 and energy delivery section 18 can be constructed from a single material as illustrated in FIG. 4A. Suitable materials include, but are not limited to polyimide, polyolefin, polyester. The entire sheath or only the sheath proximal end may be reinforced by braiding, mesh or other constructions to increase flexibility, kink resistance, and pushability. As illustrated in FIG. 4A, the drug delivery ports 58 can be included in the sheath 12. The drug delivery ports 58 can be coupled with independent drug delivery lumens 28 as illustrated in FIG. 4B.

The sheath can include a support section 17 which is constructed from a different material than the energy delivery section as illustrated in FIG. 5. FIG. 5 also illustrates the occlusion device 22 as being integral with the energy delivery section 15. The energy delivery section 18 can be constructed from a material which readily transmits ultrasound energy. The support section can be constructed from a material which provides structural strength and kink resistance. Further, the support section or the proximal end of the support section may be reinforced by braiding, mesh or other constructions to increase flexibility, kink, resistance, and pushability. Suitable materials for the support section include, but are not limited to, polyimides, polyolefin, polyester. A suitable outer diameter for the support section includes, but is not limited to 0.020" to 0.200". Suitable materials for the energy delivery section 18 include, but are not limited to, polyolefins, polyimides, polyester and other low ultrasound impedance materials. Low ultrasound impedance materials are materials which readily transmit ultrasound energy with minimal absorption of the ultrasound energy.

Figure 6A:
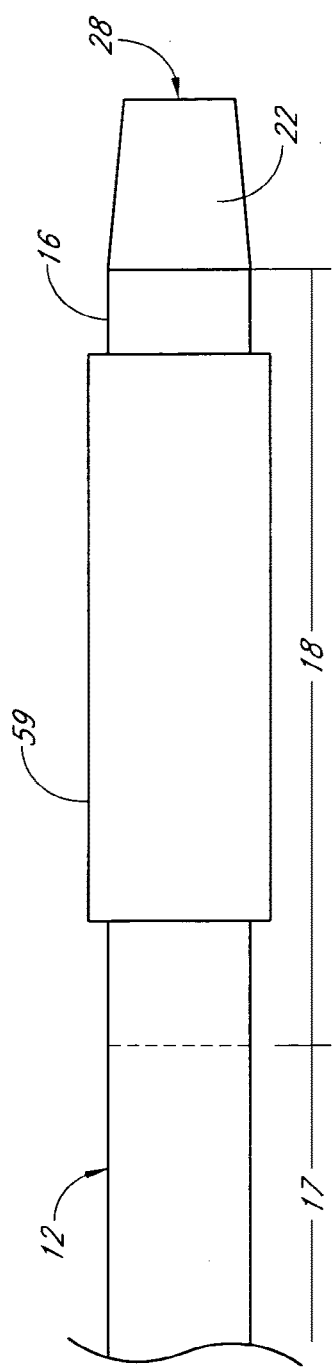
FIG. 6A is a sideview of a sheath including a balloon.

The sheath distal end 16 can include a balloon 59 as illustrated in FIG. 6A. The balloon 59 can be constructed from permeable membrane or a selectively permeable membrane which allows certain media to flow through the membrane while preventing other media from flowing through the membrane. Suitable materials for the balloon 59 include, but are not limited to cellulose, cellulose acetate, polyvinylchloride, polyolefin, polyurethane and polysulfone. When the balloon is constructed from a permeable membrane or a selectively permeable membrane, the membrane pore sizes are preferably 5 A-2 µm; more preferably 50 A-900 A and most preferably 100 A-300 A in diameter.

Figure 6B:
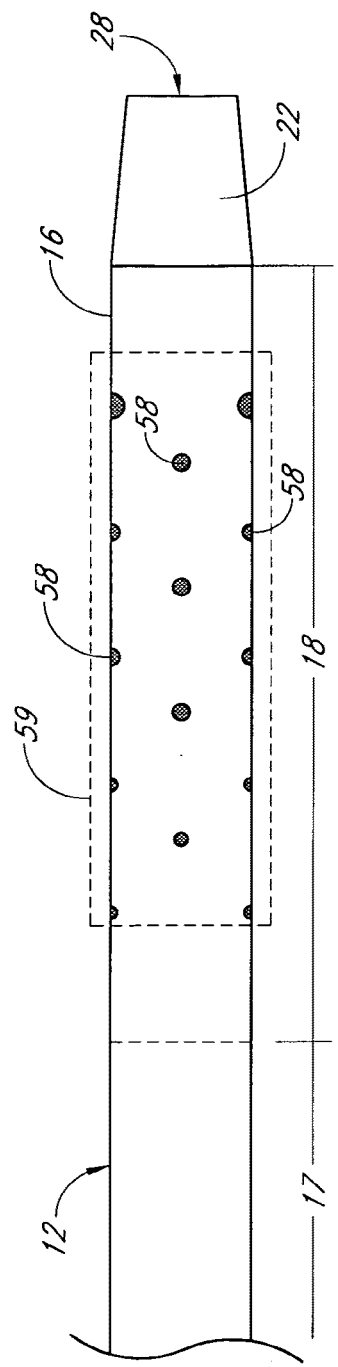
FIG. 6B is a cross section a balloon positioned at a distal end of a sheath which includes drug delivery ports configured to produce an even flow along the length of the energy delivery section.

As illustrated in FIG. 6B, the balloon 59 can be positioned adjacent drug delivery ports 5S. The drug delivery ports 58 can be designed so a uniform flow occurs along the length of the energy delivery section 15. This design can serve to prevent a pressure gradient from developing along the length of the balloon. Delivering a drug solution through the drug delivery ports 58, can serve to expand the balloon 59. When the balloon 59 is constructed from a membrane or a selectively permeable membrane, the drug solution can be delivered with enough pressure to drive the drug across the membrane. Various phoretic processes and apparatuses can also be used to drive the drug solution across the membrane. When the balloon 59 is constructed from a selectively permeable membrane, the pressure and/or phoresis may drive only certain components of the drug solution across the membrane while preventing other components from crossing the membrane.

Figure 6C:
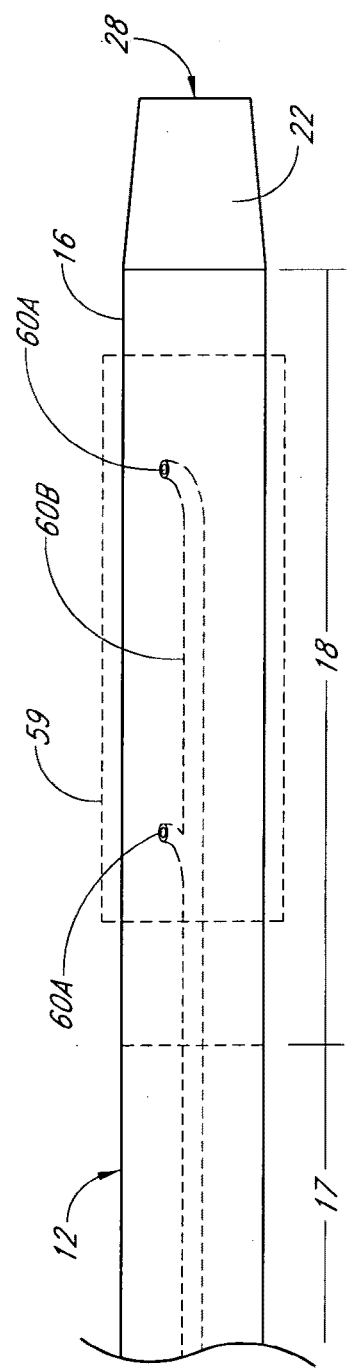
FIG. 6C is a cross section of a balloon positioned at a distal end of a sheath which includes an expansion lumen for expanding the balloon and delivering a drug solution.

The balloon 59 can also be positioned adjacent one or more expansion ports 60A coupled with an expansion lumen 60B as illustrated in FIG. 6C. The drug solution can be delivered to the balloon 59 via the expansion lumen 60B. Delivering a drug solution through the expansion lumen 60B can serve to expand the balloon 59. When the balloon 59 is constructed from a membrane or a selectively permeable membrane, the drug can be delivered with enough pressure to drive the drug solution or certain components of the drug solution across the membrane. Similarly, phoretic means can also be used to drive the drug solution or certain components of the drug solution across the membrane.

Figure 6D:
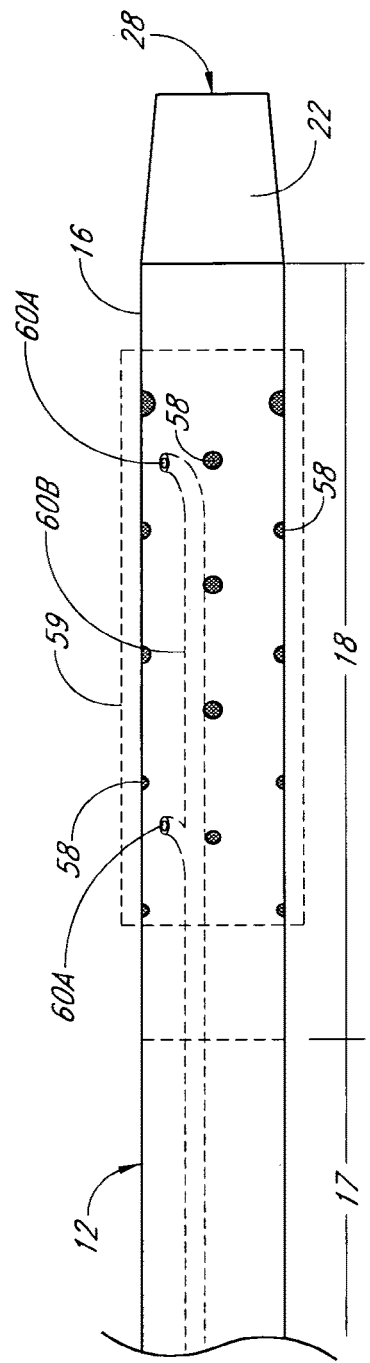
FIG. 6D is a cross section of a balloon positioned at a distal end of a sheath which includes an expansion lumen for expanding the balloon and drug delivery ports configured to produce an even flow along the length of the energy delivery section.

The balloon 59 can also be positioned adjacent expansion ports 60A coupled with an expansion lumen 60B and drug delivery ports 58 as illustrated in FIG. 6D. Different drug solutions can be delivered through the expansion ports 60B and the drug delivery ports 58. Further, a media suitable for expanding the balloon 59 can be delivered through the expansion lumen 60B and the expansion ports 60A while the drug solution can be delivered through the drug delivery ports 58. When the balloon 59 is constructed from a membrane or a selectively permeable membrane, a medium which wets the membrane and enhances the permeability of the membrane can be delivered through the expansion ports 60A. A drug solution can be delivered through the drug delivery ports 58 concurrently with or after the wetting medium has been delivered.

The ultrasound energy can be generated at an ultrasound energy source which is remote from the ultrasound elements 40 and transmitted via wire to the ultrasound elements 40. Ultrasound can also be internally generated from electrical power delivered to the ultrasound elements 40 from an electrical energy source. A suitable example of an ultrasound element 40 for internal generation of ultrasound energy includes, but is not limited to, piezoelectric ceramic oscillators. The ultrasound elements 40 can be shaped as a cylinder, a hollow cylinder and a disk which are concentric with the elongated body 34. The ultrasound elements 40 can also be an array of smaller ultrasound elements 40 or a thin plate positioned within the elongated body 34. Similarly, a single ultrasound element 40 can be composed of several smaller ultrasound elements 40. Suitable frequencies for the ultrasound element include, but are not limited to from 20 KHz to 2 MHz.

Each ultrasound element 40 can each be individually powered. When the elongated body 34 includes N ultrasound elements 40, the elongated body 34 must include 2N wires to individually power N ultrasound elements 40. The individual ultrasound elements 40 can also be electrically coupled in serial or in parallel as illustrated in FIGS. 7A and 7B. These arrangements permit maximum flexibility as they require only 2N wires. Each of the ultrasound elements 40 receive power simultaneously whether the ultrasound elements 40 are in series or in parallel. When the ultrasound elements 40 are in series, less current is required to produce the same power from each ultrasound element 40 than when the ultrasound elements 40 are connected in parallel. The reduced current allows smaller wires to be used to provide power to the ultrasound elements 40 and accordingly increases the flexibility of the elongated body 34. When the ultrasound elements 40 are connected in parallel, an ultrasound element 40 can break down and the remaining ultrasound elements 40 will continue to operate.

Figure 7C:
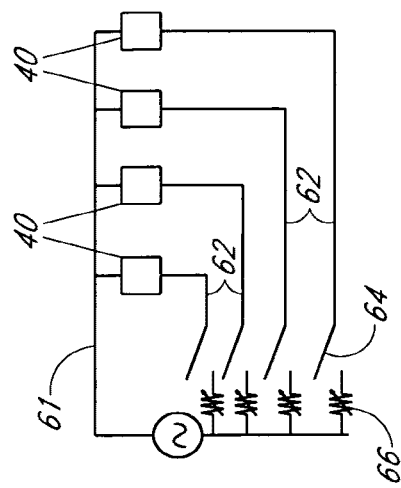
FIG. 7C illustrates ultrasound elements connected with a common wire.
Figure 7B:
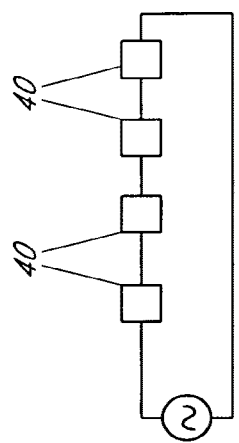
FIG. 7B illustrates ultrasound elements connected in series.
Figure 7A:
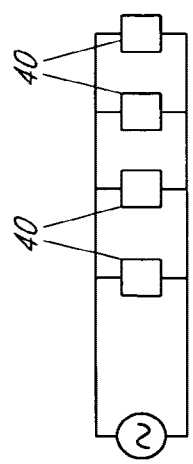
FIG. 7A illustrates ultrasound elements connected in parallel.

As illustrated in FIG. 7C, a common wire 61 can provide power to each of ultrasound element 40 while each ultrasound element 40 has its own return wire 62. A particular ultrasound element 40 can be individually activated by closing a switch 64 to complete a circuit between the common wire 61 and the particular ultrasound element's return wire 62. Once a switch 64 corresponding to a particular ultrasound element 40 has been closed, the amount of power supplied to the ultrasound element 40 can be adjusted with the corresponding potentiometer 66. Accordingly, an elongated body 34 With N ultrasound elements 40 requires only N+1 wires and still permits independent control of the ultrasound elements 40. This reduced number of wires increases the flexibility of the elongated body 34. To improve the flexibility of the elongated body 34, the individual return wires 62 can have diameters which are smaller than the common wire 61 diameter. For instance, in an embodiment where N ultrasound elements 40 will be powered simultaneously, the diameter of the individual return wires 62 can be the square root of N times smaller than the diameter of the common wire 61.

As illustrated in FIG. 1, the system 10 can include at least one temperature sensor 20. Suitable temperature sensors 20 include, but are not limited to, thermistors, thermocouples, resistance temperature detectors (RTD)s, and fiber optic temperature sensors which use thermalchromic liquid crystals. Suitable temperature sensor 20 geometries include, but are not limited to, a point, patch, stripe and a band around the sheath 12. The temperature sensors 20 can be positioned on the sheath 12 or on the elongated body 34 near the ultrasound elements 40. The temperature sensors 20 should be positioned so they are exposed to the portion of a treatment section which is receiving drug solution and/or ultrasound energy.

Figure 8:
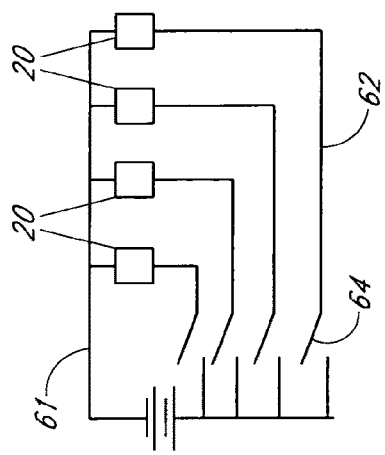
FIG. 8 illustrates temperature sensors connected with a common wire.

The temperature sensors 20 can be electrically connected as illustrated in FIG. 8. Each temperature sensor 20 can be coupled with a common wire 61 and then include its own return wire 62. Accordingly, N+1 wires can be used to independently sense the temperature at the temperature sensors 20 when N temperature sensors 20 are employed. A suitable common wire 61 can be constructed from Constantan and suitable return wires 62 can be constructed from copper. The temperature at a particular temperature sensor 20 can be determined by closing a switch 64 to complete a circuit between the thermocouple's return wire 62 and the common wire 61. When the temperature sensors 20 are thermocouples, the temperature can be calculated from the voltage in the circuit. To improve the flexibility of the sheath 12, the individual return wires 62 can have diameters which are smaller than the common wire 61 diameter.

Each temperature sensor 20 can also be independently wired. Employing N independently wired temperature sensors 20 requires 2N wires to pass the length of the sheath 12.

The sheath 12 or elongated body 34 flexibility can also be improved by using fiber optic based temperature sensors 20. The flexibility can be improved because only N fiber optics need to be employed sense the temperature at N temperature sensors 20.

Figure 9:
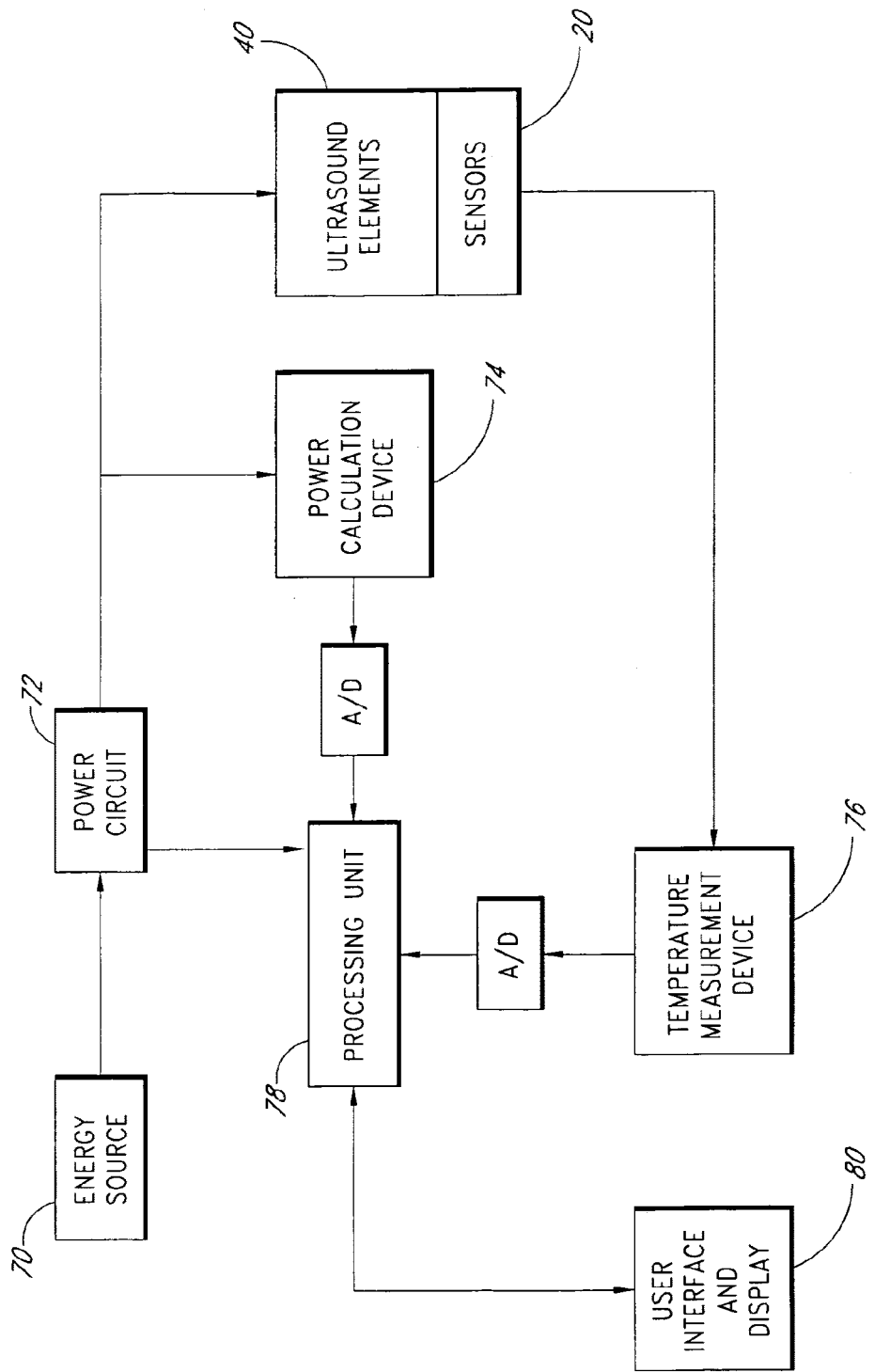
FIG. 9 is a block diagram of a feedback control system.

The system 10 can be include a feedback control system 68 as illustrated in FIG. 9. The temperature at each temperature sensor 20 is monitored and the output power of energy source adjusted accordingly. The physician can, if desired, override the closed or open loop system.

The feedback control system 68 includes an energy source 70, power circuits 72 and a power calculation device 74 coupled with the ultrasound elements 40. A temperature measurement device 76 is coupled with the temperature sensors 20 on the sheath 12. A processing unit 78 is coupled with the power calculation device 74, the power circuits 72 and a user interface and display 80.

In operation, the temperature at each temperature sensor 20 is determined at the temperature measurement device 76. The processing unit 78 receives each determined temperature from the temperature measurement device 76. The determined temperature can then be displayed to the user at the user interface and display 80.

The processing unit 78 includes logic for generating a temperature control signal. The temperature control signal is proportional to the difference between the measured temperature and a desired temperature. The desired temperature can be determined by the user. The user can set the predetermined temperature at the user interface and display 80.

The temperature control signal is received by the power circuits 72. The power circuits, 72 adjust the power level of the energy supplied to the ultrasound elements 40 from the energy source 70. For instance, when the temperature control signal is above a particular level, the power supplied to a particular ultrasound element 40 is reduced in proportion to the magnitude of the temperature control signal. Similarly, when the temperature control signal is below a particular level, the power supplied to a particular ultrasound element 40 is increased in proportion to the magnitude of the temperature control signal. After each power adjustment, the processing unit 78 monitors the temperature sensors 20 and produces another temperature control signal which is received by the power circuits 72.

The processing unit 78 can also include safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to the ultrasound elements 40.

Since, the ultrasound elements 40 may be mobile relative to the temperature sensors 20, it can be unclear which ultrasound transducer should have a power level adjustment. As a result, the power level may be identically adjusted at each ultrasound element 40. Further, the power supplied to each of the ultrasound elements 40 may be adjusted in response to the temperature sensor 20 which indicates the highest temperature. Making power adjustments in response to the temperature of the temperature sensor 20 indicating the highest temperature can prevent overheating of the treatment site.

The processing unit 78 also receives a power signal from a power calculation device 74. The power signal can be used to determine the power being received by each ultrasound element 40. The determined power can then be displayed to the user on the user interface and display 80.

The feedback control system 68 can maintain the tissue adjacent to the ultrasound elements 40 at a desired temperature for a selected period of time. As described above, the ultrasound elements 40 can be electrically connected so each ultrasound element 40 can generate an independent output. The output maintains a selected energy at each ultrasound element 40 for a selected length of time.

The processing unit 78 can be a digital or analog controller, or a computer with software. When the processing unit 78 is a computer it can include a CPU coupled through a system bus. The user interface and display 80 can be a mouse, keyboard, a disk drive, or other non-volatile memory systems, a display monitor, and other peripherals, as are known in the art. Also coupled to the bus is a program memory and a data memory.

In lieu of the series of power adjustments described above; a profile of the power delivered to each ultrasound element 40 can be incorporated in the processing unit 78 and a preset amount' of energy to be delivered may also be profiled. The power delivered to each ultrasound element 40 can be the adjusted according to the profiles.

Figure 10A:
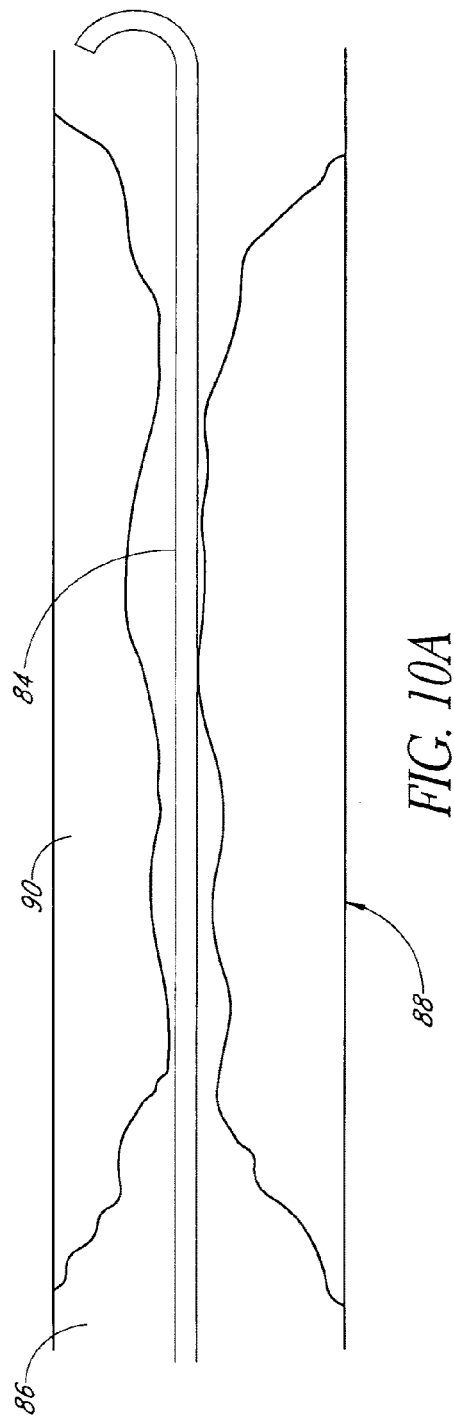
FIG. 10A is a cross section of a treatment site.

FIGS. 10A-10G illustrate a method for using the system 10. In FIG. 10A, a guidewire 84 similar to a guidewire used in typical angioplasty procedures is directed through vessels 86 toward a treatment site 88 which includes a clot 90. The guidewire 84 is directed through the clot 90. Suitable vessels include, but are not limited to, cardiovascular vessels the pancreas, sinuses, esophagus, rectum, gastrointestinal vessels and urological vessels.

Figure 10B:
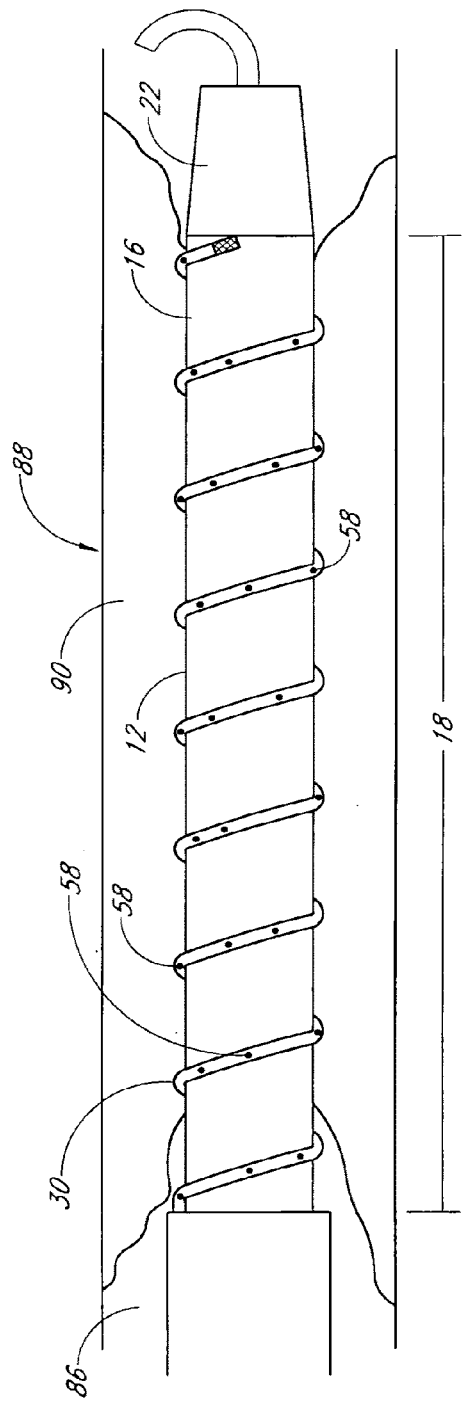
FIG. 10B is a sideview of a sheath distal end positioned at a treatment site.

In FIG. 10B, the utility lumen 28 of the sheath 12 is slid over the guidewire 84 and the sheath 12 is advanced along the guidewire 84 using traditional over-the-guidewire techniques. The sheath 12 is advanced until the energy delivery section 18 of the sheath 12 is positioned at the clot 90. Radio opaque markers may be positioned at the energy delivery section 18 of the sheath 12 to aid in the positioning of the sheath 12 within the treatment site 88.

Figure 10C:
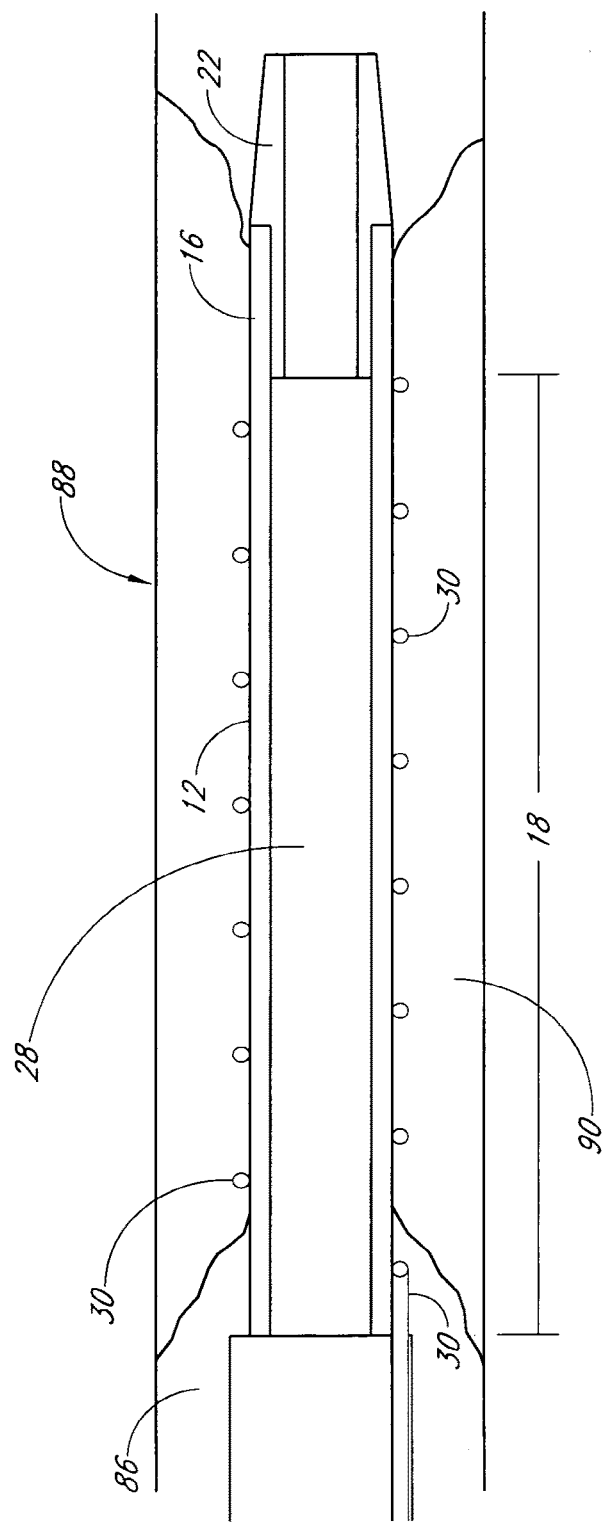
FIG. 10C is a sideview of a sheath distal end positioned at a treatment site.
Figure 10D:
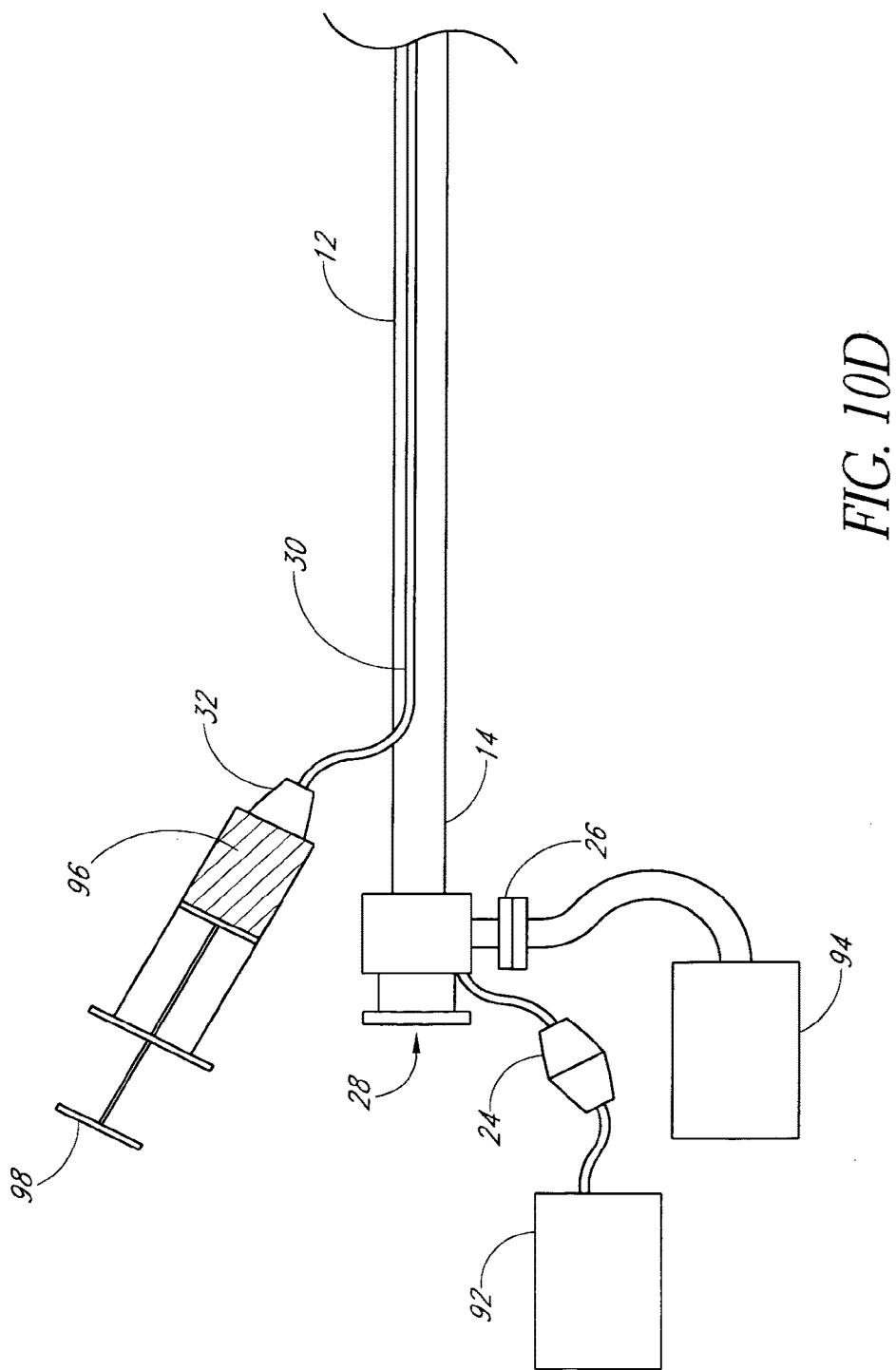
FIG. 10D is a sideview of a sheath proximal end.
Figure 10E:
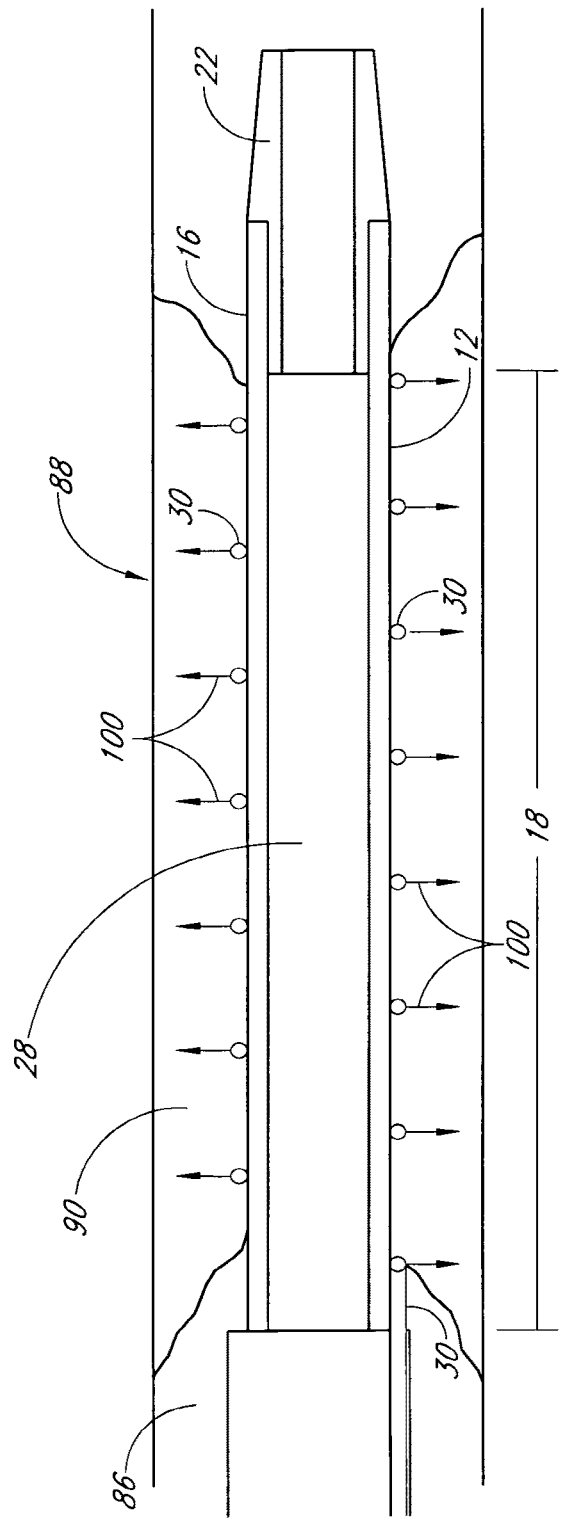
FIG. 10E is a cross section of a sheath distal end positioned at a treatment site.

In FIG. 10C, the guidewire 84 is withdrawn from the utility lumen 28 by pulling the guidewire 84 proximally while holding the sheath 12 stationary. In FIG. 10D, a temperature monitor 92 is coupled with the temperature sensor leads 24, a cooling fluid source 94 is coupled with the cooling fluid inlet and a drug solution source 96 is coupled with the drug inlet port 32. The drug solution source 96 can be a syringe with a Luer fitting which is complementary with the drug inlet port 32. Pressure can be applied to a plunger 98 on the drug solution source 96 to drive the drug solution through the drug delivery lumen 56. The drug solution is delivered from the drug delivery lumen 56 through the drug delivery ports 58 as illustrated by the arrows 100 in FIG. 10E. Suitable drug solutions include, but are not limited to, an aqueous solution containing Heparin, Uronkinase, Streptokinase, or tissue Plasminogen Activator (TPA).

Figure 10F:
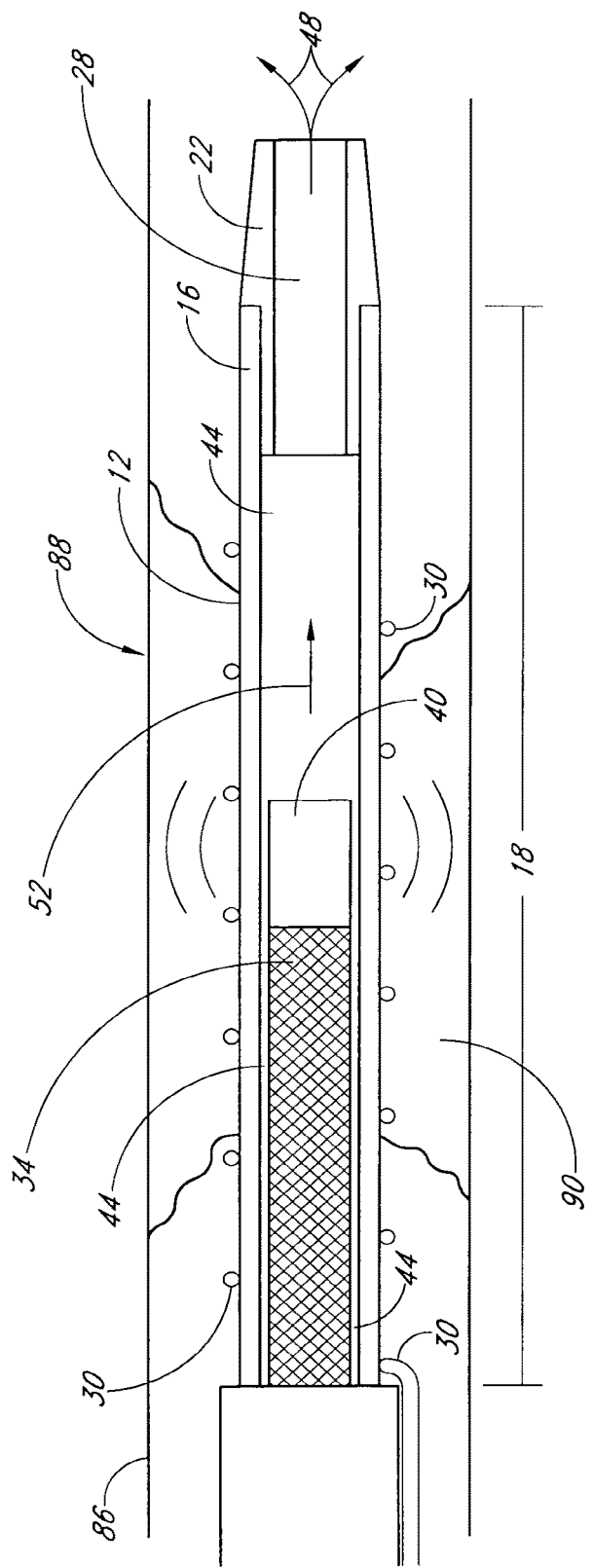
FIG. 10F illustrates an ultrasound element positioned within a utility lumen.

In FIG. 10F, the elongated body 34 is inserted into the utility lumen 28 until the ultrasound element 40 is positioned within the energy delivery section 18. To aid in placement of the ultrasound element 40 within the energy delivery section 18, radiopaque markers may be positioned on the elongated body 34 adjacent to each of the ultrasound elements 40. The ultrasound elements 40 themselves can be radiopaque. Once the elongated body 34 is properly positioned, the ultrasound element 40 is activated to deliver ultrasound energy through the energy delivery section 18 to the clot 90. Suitable ultrasound energy is delivered with a frequency from 20 KHz to 2 MHz. While the ultrasound energy is being delivered, the ultrasound element 40 can be moved within the energy delivery section 18 as illustrated by the arrows 52. The movement of the ultrasound element 40 within the energy delivery section 18 can be caused by manipulating the body proximal section while holding the sheath proximal section stationary. A cooling fluid is flowed through the cooling fluid lumen 44 and out the occlusion device 22.

Figure 10G:
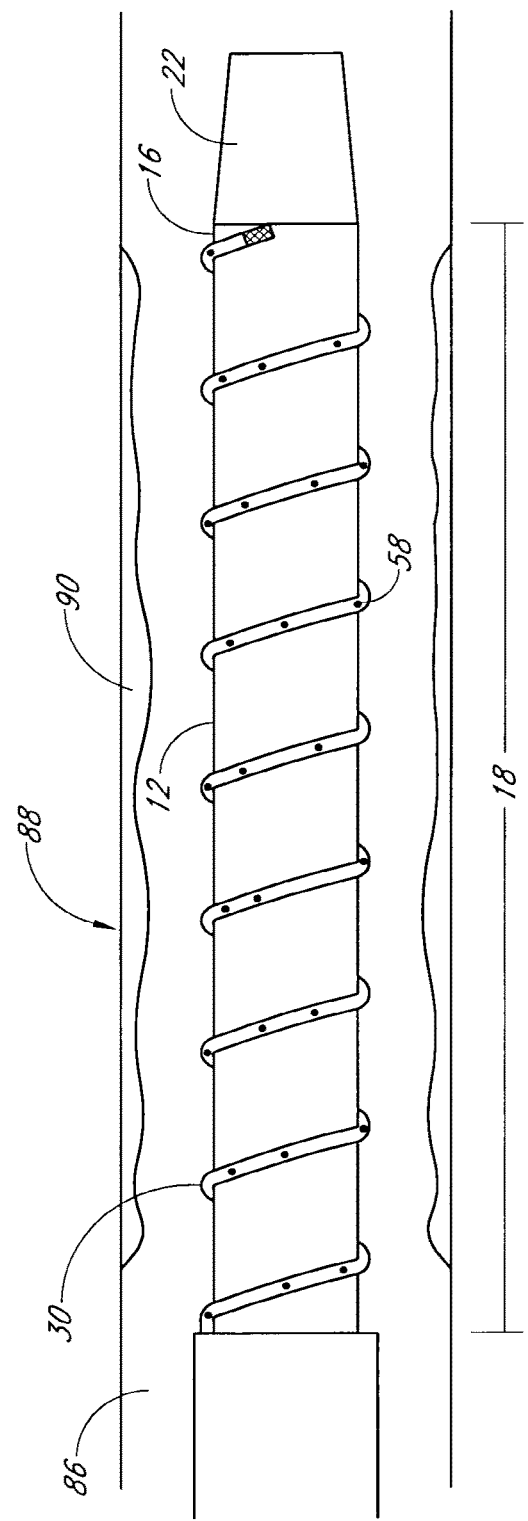
FIG. 10G is a sideview of a sheath distal end positioned at a treatment site.

The cooling fluid can be delivered before, after, during or intermittently with the delivery of the ultrasound energy. Similarly, the drug solution can be delivered before, after, during or intermittently to the delivery of ultrasound energy. As a result, the acts illustrated in FIGS. 10A-10F can be performed in different orders than are described above. The drug solution and energy are applied until the clot 90 is partially or entirely dissolved as illustrated in FIG. 10G. Once the clot 90 has been dissolved to the desired degree, the sheath 12 and elongated body 34 are withdrawn from the treatment site 88.

Figure 11A:
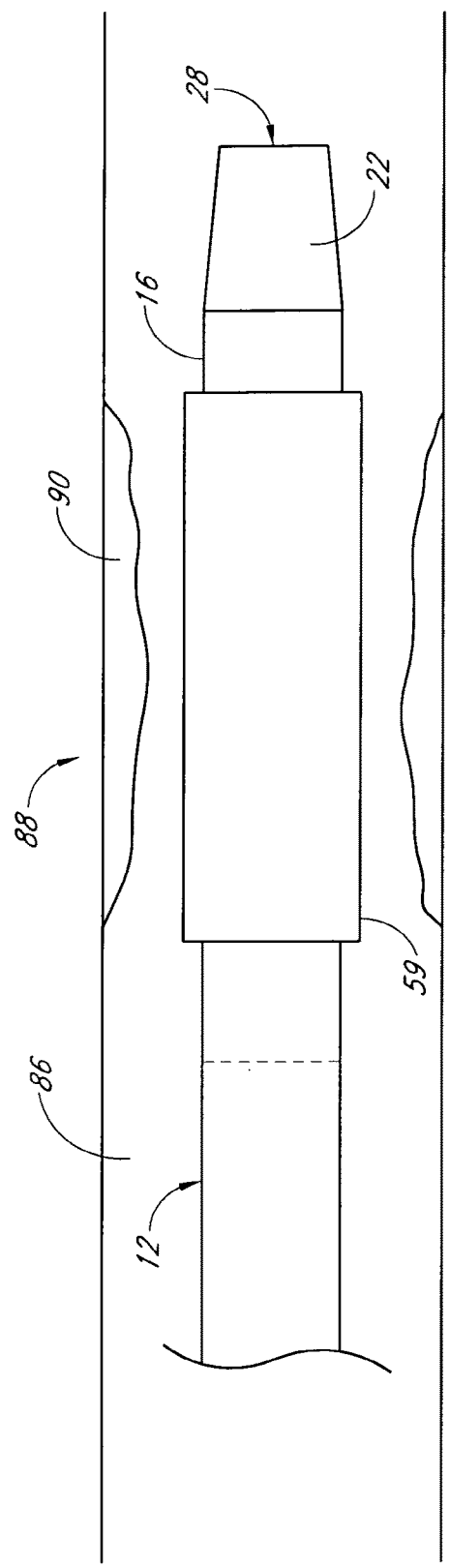
FIG. 11A illustrates a balloon positioned adjacent a clot.
Figure 11B:
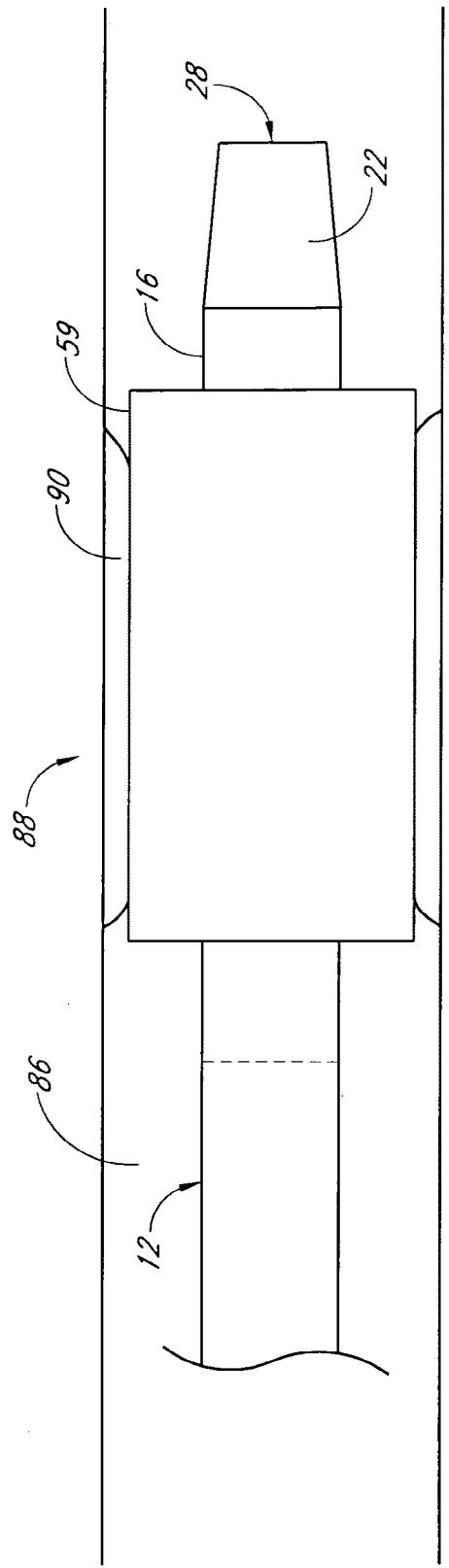
FIG. 11B illustrates a balloon expanded into contact with the clot of FIG. 11A.

FIGS. 11A-11B illustrate a method for using the system 10 when the sheath distal end 16 includes a balloon 59. The sheath 12 is advanced through a vessel 86, as described above, until the balloon 59 is positioned adjacent a clot 90 as illustrated in FIG. 11A. The balloon 59 is expanded until the balloon 59 contacts the clot 90 as illustrated in FIG. 11B. As described above, the balloon 59 can be expanded by delivering a drug solution through an expansion port 60A or a drug delivery port 58 or by delivering an expansion media through an expansion port 60A. Once the balloon 59 contacts the clot 90, the drug solution or components of the drug solution are driven across the membrane so the drug solution or the components of the drug solution contact the clot 90. The elongated body 34 can be inserted into the sheath 12 before, after or concurrently with the expansion of the balloon 59 and/or the delivery of the drug solution. Similarly, the ultrasound element 40 can be operated before, after, intermittently or concurrently with the expansion of the balloon 59 and/or the delivery of the drug solution.

The foregoing description of a preferred embodiment of the invention has been presented for purposes of illustration and description. It is not intended to be exhaustive or to limit the invention to the precise forms disclosed. Obviously, many modifications, combinations and variations will be apparent to practitioners skilled in this art.

What is claimed is:

1. An apparatus for delivering ultrasound energy and a drug solution to a treatment site within a patient's vasculature, the apparatus comprising:
   an elongate, hollow sheath having a distal opening and an energy delivery section, wherein the sheath within the energy delivery section is at least partially constructed from a material that transmits ultrasound energy;
   a drug delivery lumen positioned along at least a portion of the sheath, the drug delivery lumen having a series of drug delivery ports within the energy delivery section, the series of drug delivery ports configured to deliver drug solution to the treatment site;
   an elongate body comprising an ultrasound element, the elongate body is movably positioned within the sheath, such that ultrasonic energy can be transmitted from the ultrasound element through the energy delivery section of the sheath; and a cooling fluid lumen formed between the elongate body and the sheath by positioning the elongate body within the sheath.

2. The apparatus of claim 1, wherein the drug delivery lumen forms a portion of the sheath.

3. The apparatus of claim 1, wherein the energy delivery section comprises a material having low ultrasound absorbance.

4. The apparatus of claim 1, wherein the sheath has an outer surface with a substantially cylindrical cross-sectional profile, and wherein the drug delivery lumen is positioned within the outer surface of the sheath.

5. The apparatus of claim 1, wherein the elongate body comprises a plurality of ultrasound elements.

6. The apparatus of claim 1, further comprising a cooling fluid lumen defined by a region of the sheath not occupied by the elongate body.

7. The apparatus of claim 1, wherein the cooling fluid lumen is adjacent to the drug delivery lumen and the elongate body.

8. The apparatus of claim 1, wherein a first portion of the drug delivery lumen, located outside the energy delivery section, is not perforated, and wherein a second portion of the drug delivery lumen, located within the energy delivery section, is perforated.

9. The apparatus of claim 1, wherein a plurality of drug delivery lumens are positioned along at least a portion of the sheath.

10. An apparatus comprising:
an elongate, hollow utility lumen having a proximal region and distal region opposite the proximal region, wherein the utility lumen comprises a drug delivery lumen that extends from the proximal region to the distal region, and the drug delivery lumen comprises a plurality of drug delivery ports in the distal region; and
an elongate body comprising an ultrasound element, the elongate body is movably inserted within the utility lumen, such that the ultrasound element is positionable within the distal region of the utility lumen, and
a cooling fluid lumen defined by a region of the utility lumen not occupied by the elongate body.

11. The apparatus of claim 10, wherein at least a portion of the utility lumen distal region comprises a material having low ultrasound absorbance.

12. The apparatus of claim 10, wherein the utility lumen distal region has an outer surface with a substantially cylindrical cross-sectional profile, and wherein the drug delivery lumen is positioned within the outer surface of the utility lumen.

13. The apparatus of claim 10, wherein the elongate body comprises a plurality of ultrasound elements.

14. The apparatus of claim 10, wherein a cooling fluid lumen is form between the elongate body and the utility lumen by insertion of the elongate body into the utility lumen.

15. The apparatus of claim 10, wherein the cooling fluid lumen is adjacent to the drug delivery lumen and the elongate body.

16. The apparatus of claim 10, wherein a first portion of the drug delivery lumen, located in the proximal region of the utility lumen, is not perforated, and wherein a second portion of the drug delivery lumen, located in the distal region of the utility lumen, is perforated.

17. The apparatus of claim 10, wherein the utility lumen includes a plurality of perforated drug delivery lumens.

18. A system for delivering ultrasound energy and a drug solution to a treatment site within a patient's vasculature, the system comprising:
an elongate sheath configured to be inserted into the patient's vasculature, the elongate sheath forming a utility lumen having an energy delivery section;
a drug delivery lumen positioned along the elongate sheath, the drug delivery lumen having a plurality of perforations along the energy delivery section, such that a drug solution can be delivered into the patient's vasculature in a treatment site adjacent the energy delivery section; and
an elongate body having an ultrasound element, wherein the elongate body is insertable and movable within, the utility lumen, such that a cooling fluid lumen is formed between the elongate body and the utility lumen.

19. The system of claim 18, wherein the drug delivery lumen forms a portion of the sheath.

20. The system of claim 18, wherein the energy delivery section comprises a material having low ultrasound absorbance.

21. The system of claim 18, wherein the drug delivery lumen is positioned within the utility lumen.

22. The system of claim 18, wherein the elongate body includes a plurality of ultrasound elements.

23. The system of claim 18, wherein insertion of the elongate body into the utility lumen forms a cooling fluid lumen defined by a region of the utility lumen not occupied by the elongate body.

24. The system of claim 18, wherein insertion of the elongate body into the utility lumen forms a cooling fluid lumen adjacent to the drug delivery lumen and the elongate body.

25. The system of claim 18, wherein a first portion of the drug delivery lumen, located outside the energy delivery section, is not perforated, and wherein a second portion of the drug delivery lumen, located within the energy delivery section, is perforated.

26. The system of claim 18, wherein a plurality of drug delivery lumens are positioned along the elongate sheath.

27. The apparatus of claim 1, wherein a first portion of the drug delivery lumen located within the energy delivery section is external to the sheath.

28. The apparatus of claim 27, wherein a second portion of the drug delivery lumen located outside the energy delivery section is incorporated into the sheath.

29. The apparatus of claim 27, wherein a second portion of the drug delivery lumen located outside the energy delivery section is external to the sheath.

30. The apparatus of claim 1, wherein the series of drug delivery ports have different sizes.

31. The apparatus of claim 1, wherein the drug delivery lumen is wound around the energy delivery section.

32. The apparatus of claim 1, wherein the density of the series of drug delivery ports changes along the length of the energy delivery section.

33. The apparatus of claim 1, wherein the series of drug delivery ports are slits.

* * * * *

UNITED STATES PATENT AND TRADEMARK OFFICE
CERTIFICATE OF CORRECTION

| | | |
|---|---|---|
| PATENT NO. | : 8,764,700 B2 | Page 1 of 1 |
| APPLICATION NO. | : 13/332226 | |
| DATED | : July 1, 2014 | |
| INVENTOR(S) | : John Zhang et al. | |

It is certified that error appears in the above-identified patent and that said Letters Patent is hereby corrected as shown below:

In the Specification,

In column 6 at line 18, Change "20," to --2D,--.

In column 7 at line 54, Change "15." to --18.--.

In column 8 at line 16, Change "5S." to --58.--.

In column 8 at line 18, Change "15." to --18.--.

In the Claims,

In column 13 at line 53, in Claim 14, change "form" to --informed--.

Signed and Sealed this
Twenty-fourth Day of February, 2015

Michelle K. Lee
*Deputy Director of the United States Patent and Trademark Office*